(12) United States Patent
Denison et al.

(10) Patent No.: US 6,673,615 B2
(45) Date of Patent: *Jan. 6, 2004

(54) CHARACTERIZATION OF INDIVIDUAL POLYMER MOLECULES BASED ON MONOMER-INTERFACE INTERACTIONS

(75) Inventors: Timothy J. Denison, Andover, MA (US); Alexis Sauer, Brighton, MA (US); Jene Golovchenko, Lexington, MA (US); Amit Meller, Newton, MA (US); Eric Brandin, Portsmouth, NH (US); Daniel Branton, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/079,178

(22) Filed: Feb. 20, 2002

(65) Prior Publication Data

US 2003/0044816 A1 Mar. 6, 2003

Related U.S. Application Data

(63) Continuation of application No. 09/457,959, filed on Dec. 9, 1999, now Pat. No. 6,362,002, which is a continuation-in-part of application No. 09/098,142, filed on Jun. 16, 1998, now Pat. No. 6,015,714, which is a continuation-in-part of application No. 08/405,735, filed on Mar. 17, 1995, now Pat. No. 5,795,782.

(51) Int. Cl.[7] .............................................. G01N 33/483
(52) U.S. Cl. ............................... 436/2; 436/151; 435/6
(58) Field of Search .......................... 436/5, 151; 435/6

(56) References Cited

U.S. PATENT DOCUMENTS

| | | | |
|---|---|---|---|
| 5,376,878 A | 12/1994 | Fisher | ........................ 324/71.4 |
| 5,795,782 A | 8/1998 | Church et al. | .................. 436/2 |
| 6,015,714 A | 1/2000 | Baldarelli et al. | .............. 436/2 |
| 6,362,002 B1 | 3/2002 | Denison et al. | |

FOREIGN PATENT DOCUMENTS

| | | |
|---|---|---|
| DE | 3028569 A1 | 2/1982 |
| GB | 2 232 769 A | 12/1990 |
| WO | WO 94/25862 | 11/1994 |

OTHER PUBLICATIONS

Auld et al., "A Neutral Amino Acid Change in Segment IIS4 Dramatically Alters the Gating Properties of the Voltage–Dependent Sodium Channel", 1990, *Proc. Natl. Acad. Sci. USA*, 87:323–27.
Bensimon, A., et al., "Alignment and Sensitive Detection of DNA by a Moving Interface", 1994, *Science*, 265: 2096–98.
Benz et al., "Pore Formation by LamB of *Escherichia coli* in Lipid Bilayer Membranes", 1986, *J. Bacteriology*, 165(3):978–86.
Benz et al., "Mechanism of Sugar Transplant through the Sugar–Specific LamB Channel of *Escherichia coli* Outer Membrane", 1987, *J. Membrane Biol.*, 100:21–29.
Bezrukov et al., "Counting Polymers Moving Through a Single Ion Channel", 1994, *Nature*, 370:279–81.
Boulain et al., "Mutagenesis by Random Linker Insertion into the LamB Gene of *Escherichia coli* K12", 1986, *Mol. Gen. Genet.*, 205:339–48.
Boulanger et al., "Characterization of Ion Channels Involved in the Penetration of Phage T4 DNA into *Escherichia coli* Cells", 1988, *J. Biolog. Chem.*, 263(20)9767–75.
Boulanger et al., "Ion Channels Are Likely to Be Involved in the Two Steps of Phage T5 DNA Penetration into *Escherichia coli* Cells", 1992, *J. Biolog. Chem.*, 267(5):3168–72.
Boyd et al., "Determinants of Membrane Protein Topology", 1987, *Proc. Natl. Acad. Sci. USA*, 84:8525–29.
Charbit et al., "Permissive Sites and Topology of an Outer Membrane Protein with a Reporter Epitope", 1991, *J. Bacteriology*, 173(1):262–75.
Dargent et al., "Selectivity for Maltose and Maltodextrins of Maltoporin, a Pore–Forming Protein of *E. coli* Outer Membrane", 1987, *FEBS Letters*, 220(1):136–42.
Dargent et al., "Effect of Point Mutations on the in–Vitro Pore Properties of Maltoporin, a Protein of *Escherichia coli* Outer Membrane", 1988, *J. Mol. Biol.*, 201:497–506.
DeBlois et al., "Electrokinetic Measurements with Submicron Particles and Pores by the Resistive Pulse Technique", 1977, *J. Colloid and Interface Science*, 61(2);323–35.
Ehrmann et al., "Genetic Analysis of Membrane Protein Topology by a Sandwich Gene Fusion Approach", 1990, *Proc. Natl. Acad. Sci. USA*, 87:7574–78.
Ferenci et al., "Channel Architecture in Maltoporin: Dominance Studies with LamB Mutations Influencing Maltodextrin Binding Provide Evidence for Independent Selectivity Filters in Each Subunit", 1989, *J. Bacteriology*, 171(2):855–61.
Ghadiri et al., "Artificial Transmembrane Ion Channels From Self–Assembling Peptide Nanotubes", 1994, *Nature*, 369:301–304.
Hall et al., "Alamethicin: A Rich Model for Channel Behavior", 1984, *J. Biophys.*, 45:233–47.

(List continued on next page.)

Primary Examiner—Charles L. Patterson, Jr.
(74) Attorney, Agent, or Firm—Hale and Dorr LLP

(57) ABSTRACT

The invention relates to a method for detecting a double-stranded region in a nucleic acid by (1) providing two separate, adjacent pools of a medium and a interface between the two pools, the interface having a channel so dimensioned as to allow sequential monomer-by-monomer passage of a single-stranded nucleic acid, but not of a double-stranded nucleic acid, from one pool to the other pool; (2) placing a nucleic acid polymer in one of the two pools; and (3) taking measurements as each of the nucleotide monomers of the single-stranded nucleic acid polymer passes through the channel so as to differentiate between nucleotide monomers that are hybridized to another nucleotide monomer before entering the channel and nucleotide monomers that are not hybridized to another nucleotide monomer before entering the channel.

10 Claims, 14 Drawing Sheets

OTHER PUBLICATIONS

Hamill et al., "Improved Patch–Clamp Techniques for High–Resolution Current Recording from Cells and Cell–Free Membrane Patches", 1981, *Pflügers Archiv. Eur. J. Physiology*, 391(2):85–100.

Harrington et al., "The F Pilus of *Escherichia coli* Appears to Support Stable DNA Transfer in the Absence of Wall–to–Wall Contact Between Cells", 1990, *J. Bacteriology*, 172(12):7263–64.

Heinemann et al., "Open Channel Noise IV: Estimation of Rapid Kinetics of Formamide Block in Gramicidin A Channels", 1988, *J. Biophys.*, 54:757–64.

Heinemann et al., "Open Channel Noise V: Fluctuating Barriers to Ion Entry in Gramicidin A Channels", 1990, *J. Biophys.*, 57:499–514.

Henry et al., "Blockade of a Mitochondrial Cationic Channel by an Addressing Peptide: An Electrophysiological Study", 1989, *J. Membrane Biol.*, 112:139–47.

Hoshi et al., "Biophysical and Molecular Mechanisms of Shaker Potassium Channel Inactivation", 1990, *Science*, 250:533–38.

Hoshi et al., "Two Types of Inactivation in Shaker $K^+$ Channels: Effects of Alterations in the Carboxy–Terminal Region", 1991, *Neuron*, 7:547–56.

Kubitschek, "Electronic Counting and Sizing of Bacteria", *Nature*, 1958, 182:234–35.

Lakey et al., "The Voltage–Dependent Activity of *Escherichia coli* Porins in Different Planar Bilayer Reconstitutions", 1989, *Eur. J. Biochem.*, 186:303–308.

Lopez et al., "Hydrophobic Substitution Mutations in the S4 Sequence Alter Voltage–Dependent Gating in Shaker $K^+$ Channels", 1991, *Neuron*, 7:327–36.

Moellerfeld et al., "Improved Stability of Black Lipid Membranes by Coating with Polysaccharide Derivatives Bearing Hydrophobic Anchor Groups", 1986, *Biochimica et Biophysica Acta*, 857:265–70.

Nath et al., "Transcription by T7 RNA Polymerase Using benzo[a]pyrene–modified templates", 1991, *Carcinogenesis*, 12(6):973–76.

Neher et al., "Single–Channel Currents Recorded from Membrane of Denervated Frog Muscle Fibres", 1976, *Nature*, 260:799–801.

Novick et al., "Fluorescence Measurement of the Kinetics of DNA Injection by Bacteriophage λ into Liposomes", 1988, *Biochemistry*, 27:7919–24.

Ollis et al., "Domain of *E. coli* DNA Polymerase I Showing Sequence Homology to T7 DNA Polymerase", 1985, *Nature*, 313:818–19.

Ollis et al., "Structure of Large Fragment of *Escherichia coli* DNA Polymerase I Complexed with dTMP", 1985, *Nature*, 313:762–66.

Ovchinnikov et al., 3. The Cyclic Peptides: Structure, Conformation, and Function: P. Gramicidin S. (851), Its Analogs and Tyrocidines A–C (904–906), 1982, *The Proteins, Third Edition*, 5:547–55.

Ovchinnikov et al., 3. The Cyclic Peptides: Structure, Conformation, and Function: T. Valinomycin (913), 1982, *The Proteins, Third Edition*, 5:563–73.

Patton et al., "Amino Acid Residues Required for Fast $Na^+$ –channel Inactivation: Charge Neutralizations and Deletions in the III–IV Linker", 1992, *Proc. Natl. Acad. Sci. USA*, 89:10905–909.

Shiver et al., "On the Explanation of the Acidic pH Requirement for In Vitro Activity of Colicin E1", 1987, *J. Biological Chem.*, 262(29):14273–281.

Sigworth et al., "Open Channel Noise: III. High Resolution Recordings Show Rapid Current Fluctuations in Gramicidin A and Four Chemical Analogues", 1987, *J. Biophys.*, 52:1055–64.

Simon et al., "A Protein Conducting Channel in the Endoplasmic Reticulum", *Cell*, 65:371–80.

Taylor et al., "Reversed Alamethicin Conductance in Lipid Bilayers", 1991, *J. Biophys.*, 59:873–79.

Weiss et al., "Molecular Architecture and Electrostatic Properties of a Bacterial Porin", 1991, *Science*, 254:1627–30.

West et al., "A Cluster of Hydrophobic Amino Acid Residues Required for Fast $Na^+$ –channel Inactivation", 1992, *Proc. Natl. Acad. Sci. USA*, 89:10910–14.

Wonderlin et al., "Optimizing Planar Lipid Bilayer Single–Channel Recordings for High Resolution with Rapid Voltage Steps", 1990, *J. Biophys.*, 58:289–97.

Kasianowicz et al., "Characterization of Individual Polynucleotide Molecules Using a Membrane Channel" *Proc. Natl. Acad. Sci. USA* 93:13770–13773 (Nov. 1996).

Yager. "Biosensors from Membrane Proteins Reconstituted in Polymerized Lipid Bilayers." United States Statutory Invention Registration, Reg. No. H201, Jan. 6, 1987.

POLY C + POLY A

CHARACTERIZATION OF INDIVIDUAL POLYMER MOLECULES BASED ON MONOMER-INTERFACE INTERACTIONS

CROSS REFERENCE TO RELATED APPLICATIONS

This application is a continuation of U.S. application Ser. No. 09/457,959, filed Dec. 9, 1999, now U.S. Pat. No. 6,362,002; which is a continuation-in-part of U.S. application Ser. No. 09/098,142, filed Jun. 16, 1998, now U.S. Pat. No. 6,015,714; which is a continuation-in-part of U.S. application Ser. No. 08/405,735, filed Mar. 17, 1995, now U.S. Pat. No. 5,795,782.

STATEMENT AS TO FEDERALLY SPONSORED RESEARCH

This invention was made with Government support under NIH grant 1R21HG00811-01 and 5R21HG01360-02-01 awarded by the Public Health Service and grant MCB-9421831 awarded by the National Science Foundation. In addition, this invention was made with support from the National Institute of Standards and Technology. The Government has certain rights in the invention.

BACKGROUND OF THE INVENTION

Rapid, reliable, and inexpensive characterization of polymers, particularly nucleic acids, has become increasingly important. One notable project, known as the Human Genome Project, has as its goal sequencing the entire human genome, which is over three billion nucleotides.

Typical current nucleic acid sequencing methods depend either on chemical reactions that yield multiple length DNA strands cleaved at specific bases, or on enzymatic reactions that yield multiple length DNA strands terminated at specific bases. In each of these methods, the resulting DNA strands of differing length are then separated from each other and identified in strand length order. The chemical or enzymatic reactions, as well as the technology for separating and identifying the different length strands, usually involve tedious, repetitive work. A method that reduces the time and effort required would represent a highly significant advance in biotechnology.

SUMMARY OF THE INVENTION

The invention relates to a method for rapid, easy characterization of individual polymer molecules, for example polymer size or sequence determination. Individual molecules in a population may be characterized in rapid succession.

Stated generally, the invention features a method for evaluating a polymer molecule which includes linearly connected (sequential) monomer residues. Two separate pools of a medium and an interface between the pools are provided. The interface between the pools is capable of interacting sequentially with the individual monomer residues of a single polymer present in one of the pools. Interface-dependent measurements are continued over time, as individual monomer residues of a single polymer interact sequentially with the interface, yielding data suitable to infer a monomer-dependent characteristic of the polymer. Several individual polymers, e.g., in a heterogenous mixture, can be characterized or evaluated in rapid succession, one polymer at a time, leading to characterization of the polymers in the mixture.

The method is broadly useful for characterizing polymers that are strands of monomers which, in general (if not entirely), are arranged in linear strands. The method is particularly useful for characterizing biological polymers such as deoxyribonucleic acids, ribonucleic acids, polypeptides, and oligosaccharides, although other polymers may be evaluated. In some embodiments, a polymer which carries one or more charges (e.g., nucleic acids, polypeptides) will facilitate implementation of the invention.

The monomer-dependent characterization achieved by the invention may include identifying physical characteristics such as the number and composition of monomers that make up each individual molecule, preferably in sequential order from any starting point within the polymer or its beginning or end. A heterogenous population of polymers may be characterized, providing a distribution of characteristics (such as size) within the population. Where the monomers within a given polymer molecule are heterogenous, the method can be used to determine their sequence.

The interface between the pools is designed to allow passage of the monomers of one polymer molecule in single file order, that is, one monomer at a time. As described in greater detail below, the useful portion of the interface may be a passage in or through an otherwise impermeable barrier, or it may be an interface between immiscible liquids.

The medium used in the invention may be any fluid that permits adequate polymer mobility for interface interaction. Typically, the medium will be liquids, usually aqueous solutions or other liquids or solutions in which the polymers can be distributed. When an electrically conductive medium is used, it can be any medium which is able to carry electrical current. Such solutions generally contain ions as the current conducting agents, e.g., sodium, potassium, chloride, calcium, cesium, barium, sulfate, or phosphate. Conductance across the pore or channel is determined by measuring the flow of current across the pore or channel via the conducting medium. A voltage difference can be imposed across the barrier between the pools by conventional means. Alternatively, an electrochemical gradient may be established by a difference in the ionic composition of the two pools of medium, either with different ions in each pool, or different concentrations of at least one of the ions in the solutions or media of the pools. In this embodiment of the invention, conductance changes are measured and are indicative of monomer-dependent characteristics.

The term "ion permeable passages" used in this embodiment of the invention includes ion channels, ion-permeable pores, and other ion-permeable passages, and all are used herein to include any local site of transport through an otherwise impermeable barrier. For example, the term includes naturally occurring, recombinant, or mutant proteins which permit the passage of ions under conditions where ions are present in the medium contacting the channel or pore. Synthetic pores are also included in the definition. Examples of such pores can include, but are not limited to, chemical pores formed, e.g., by nystatin, ionophores, or mechanical perforations of a membranous material. Proteinaceous ion channels can be voltage-gated or voltage independent, including mechanically gated channels (e.g., stretch-activated $K^+$ channels), or recombinant engineered or mutated voltage dependent channels (e.g., $Na^+$ or $K^+$ channels constructed as is known in the art).

Another type of channel is a protein which includes a portion of a bacteriophage receptor which is capable of binding all or part of a bacteriophage ligand (either a natural or functional ligand) and transporting bacteriophage DNA from one side of the interface to the other. The polymer to be characterized includes a portion which acts as a specific ligand for the bacteriophage receptor, so that it may be injected across the barrier/interface from one pool to the other.

The protein channels or pores of the invention can include those translated from one or more natural and/or recombinant DNA molecule(s) which includes a first DNA which encodes a channel or pore forming protein and a second DNA which encodes a monomer-interacting portion of a monomer polymerizing agent (e.g., a nucleic acid polymerase or exonuclease). The expressed protein or proteins are capable of non-covalent association or covalent linkage (any linkage herein referred to as forming an "assemblage" of "heterologous units"), and when so associated or linked, the polymerizing portion of the protein structure is able to polymerize monomers from a template polymer, close enough to the channel forming portion of the protein structure to measurably affect ion conductance across the channel. Alternatively, assemblages can be formed from unlike molecules, e.g., a chemical pore linked to a protein polymerase; these assemblages fall under the definition of a "heterologous" assemblage.

The invention also includes the recombinant fusion protein(s) translated from the recombinant DNA molecule(s) described above, so that a fusion protein is formed which includes a channel forming protein linked as described above to a monomer-interacting portion of a nucleic acid polymerase. Preferably, the nucleic acid polymerase portion of the recombinant fusion protein is capable of catalyzing polymerization of nucleotides. Preferably, the nucleic acid polymerase is a DNA or RNA polymerase, more preferably T7 RNA polymerase.

The polymer being characterized may remain in its original pool, or it may cross the passage. Either way, as a given polymer molecule moves in relation to the passage, individual monomers interact sequentially with the elements of the interface to induce a change in the conductance of the passage. The passages can be traversed either by polymer transport through the central opening of the passage so that the polymer passes from one of the pools into the other, or by the polymer traversing across the opening of the passage without crossing into the other pool. In the latter situation, the polymer is close enough to the channel for its monomers to interact with the passage and bring about the conductance changes which are indicative of polymer characteristics. The polymer can be induced to interact with or traverse the pore, e.g., as described below, by a polymerase or other template-dependent polymer replicating catalyst linked to the pore which draws the polymer across the surface of the pore as it synthesizes a new polymer from the template polymer, or by a polymerase in the opposite pool which pulls the polymer through the passage as it synthesizes a new polymer from the template polymer. In such an embodiment, the polymer replicating catalyst is physically linked to the ion-permeable passage, and at least one of the conducting pools contains monomers suitable to be catalytically linked in the presence of the catalyst. A "polymer replicating catalyst," "polymerizing agent" or "polymerizing catalyst" is an agent that can catalytically assemble monomers into a polymer in a template dependent fashion—i.e., in a manner that uses the polymer molecule originally provided as a template for reproducing that molecule from a pool of suitable monomers. Such agents include, but are not limited to, nucleotide polymerases of any type, e.g., DNA polymerases, RNA polymerases, tRNA and ribosomes.

The characteristics of the polymer can be identified by the amplitude or duration of individual conductance changes across the passage. Such changes can identify the monomers in sequence, as each monomer will have a characteristic conductance change signature. For instance, the volume, shape, or charges on each monomer will affect conductance in a characteristic way. Likewise, the size of the entire polymer can be determined by observing the length of time (duration) that monomer-dependent conductance changes occur. Alternatively, the number of monomers in a polymer (also a measure of size) can be determined as a function of the number of monomer-dependent conductance changes for a given polymer traversing a passage. The number of monomers may not correspond exactly to the number of conductance changes, because there may be more than one conductance level change as each monomer of the polymer passes sequentially through the channel. However, there will be a proportional relationship between the two values which can be determined by preparing a standard with a polymer of known sequence.

The mixture of polymers used in the invention does not need to be homogenous. Even when the mixture is heterogenous, only one molecule interacts with a passage at a time, yielding a size distribution of molecules in the mixture, and/or sequence data for multiple polymer molecules in the mixture.

In other embodiments, the channel is a natural or recombinant bacterial porin molecule that is relatively insensitive to an applied voltage and does not gate. Preferred channels for use in the invention include the α-hemolysin toxin from *S. aureus* and maltoporin channels.

In other preferred embodiments, the channel is a natural or recombinant voltage-sensitive or voltage gated ion channel, preferably one which does not inactivate (whether naturally or through recombinant engineering as is known in the art). "Voltage sensitive" or "gated" indicates that the channel displays activation and/or inactivation properties when exposed to a particular range of voltages.

In an alternative embodiment of the invention, the pools of medium are not necessarily conductive, but are of different compositions so that the liquid of one pool is not miscible in the liquid of the other pool, and the interface is the immiscible surface between the pools. In order to measure the characteristics of the polymer, a polymer molecule is drawn through the interface of the liquids, resulting in an interaction between each sequential monomer of the polymer and the interface. The sequence of interactions as the monomers of the polymer are drawn through the interface is measured, yielding information about the sequence of monomers that characterize the polymer. The measurement of the interactions can be by a detector that measures the deflection of the interface (caused by each monomer passing through the interface) using reflected or refracted light, or a sensitive gauge capable of measuring intermolecular forces. Several methods are available for measurement of forces between macromolecules and interfacial assemblies, including the surface forces apparatus (Israelachvili, *Intermolecular and Surface Forces*, Academic Press, New York, 1992), optical tweezers (Ashkin et al., *Oppt. Lett.,* 11:288, 1986; Kuo and Sheetz, *Science,* 260:232, 1993; Svoboda et al., *Nature* 365:721, 1993), and atomic force microscopy (Quate, F. *Surf. Sci.* 299:980, 1994; Mate et al., *Phys. Rev. Lett.* 59:1942, 1987; Frisbie et al., *Science* 265:71, 1994; all hereby incorporated by reference).

The interactions between the interface and the monomers in the polymer are suitable to identify the size of the polymer, e.g., by measuring the length of time during which the polymer interacts with the interface as it is drawn across the interface at a known rate, or by measuring some feature of the interaction (such as deflection of the interface, as described above) as each monomer of the polymer is sequentially drawn across the interface. The interactions can also be sufficient to ascertain the identity of individual monomers in the polymer.

The invention further features a method for sequencing a nucleic acid polymer, which can be double stranded or single stranded, by (1) providing two separate, adjacent pools of a medium and an interface (e.g., a lipid bilayer) between the two pools, the interface having a channel (e.g., bacterial porin molecules) so dimensioned as to allow sequential monomer-by-monomer passage from one pool to another of only one nucleic acid polymer at a time; (2) placing the nucleic acid polymer to be sequenced in one of the two pools; and (3) taking measurements (e.g., ionic flow measurements, including measuring duration or amplitude of ionic flow blockage) as each of the nucleotide monomers of the nucleic acid polymer passes through the channel, so as to determine the sequence of the nucleotides in the nucleic acid polymer. The interface can include more than one channel in this method. In some cases, the nucleic acid polymer can interact with an inner surface of the channel. The sequencing of a nucleic acid, as used herein, is not limited to identifying specific nucleotide monomers, but can include distinguishing one type of monomer from another type of monomer (e.g., purines from pyrimidines), or distinguish one polymer from another polymer, where the two polymers differ in their nucleotide sequence.

The invention also features a method for detecting a single-stranded or double-stranded region in a nucleic acid by (1) providing two separate, adjacent pools of a medium and an interface (e.g., a lipid bilayer) between the two pools, the interface having a channel (e.g., a bacterial porin molecule) so dimensioned as to readily allow sequential monomer-by-monomer passage of a single-stranded nucleic acid, but not of a double-stranded nucleic acid, from one pool to another; (2) placing the nucleic acid to be sequenced in one of the two pools; and (3) taking measurements (e.g., ionic flow measurements, including measuring duration or magnitude of ionic flow blockage) as each of the nucleotide monomers of the single-stranded nucleic acid polymer passes through the channel so as to differentiate between nucleotide monomers that are hybridized to another nucleotide monomer before entering the channel and nucleotide monomers that are not hybridized to another nucleotide monomer before entering the channel. The interface can include more than one channel in this method. In some cases, the nucleic acid polymer can interact with an inner surface of the channel. The double-stranded region detected can be intermolecular (i.e., hybridization between two nucleic acid molecules) or intramolecular (i.e., hybridization between portions of the same nucleic acid). In addition, the method can be facilitated by varying the applied voltage across the interface, e.g., between the predetermined voltages of 120 mV and 240 mV.

The method described immediately above is especially useful for detecting hybridization, or lack thereof, of a probe to a target nucleic acid that differs from the sequence of the probe by only one nucleotide. In other words, the method can be used to detect single nucleotide alternations or mutations in the target by detecting hybridization of a probe to a target, such measurements being able to distinguish between a sequence that is exactly complementary to a probe (or a portion of the target). To facilitate this level of sensitivity, the temperature of the two pools can be set to lie half-way between the Tm of perfectly complementary probe and target and the Tm of the imperfectly complementary probe and target (e.g., between about 26° C. to 30° C. [see FIG. 12]) to achieve the necessary level of performance. Consequently, the invention also includes a method for evaluating a polymer (e.g., a nucleic acid) by (1) providing two separate pools of a medium and a interface between the two pools; (2) placing a first and second polymer in one of the two pools; (3) taking a first interface-dependent measurement over time at a first temperature as individual monomer residues of the first polymer interacts with the interface, yielding data suitable to determine a monomer-dependent characteristic of the polymer molecule; (4) adjusting the temperature of at least one of the two pools to a second temperature; and (5) taking a second interface-dependent measurement over time at the second temperature as individual monomer residues of the second polymer interacts with the interface, yielding data suitable to determine a monomer-dependent characteristic of the polymer molecule. In addition, the first and second interface-dependent measurements can be compared. When taking the second interface-dependent measurement, the polymer interacting with the interface can be the same molecule (i.e., have the same chemical structure) from which the first interface-dependent measurement was taken, or a different molecule (i.e., having a different chemical structure).

The two pools can contain an electrically conductive medium (e.g., an aqueous solution), in which case a voltage can be optionally applied across the interface to facilitate movement of the nucleic acid polymer through the channel and the taking of measurements. Such measurements are interface-dependent, i.e., the measurements are spatially or temporally related to the interface. For example, ionic measurements can be taken when the polymer traverses an internal limiting (in size or conductance) aperture of the channel. In this case, the flow of ions through the channel, and especially through the limiting aperture of the channel, is affected by the size or charge of the polymer and the inside surface of the channel. These measurements are spatially related to the interface because one measures the ionic flow through the interface as specific monomers pass a specific portion (the limiting aperture) of the interface channel.

To maximize the signal to noise ratio when ionic flow measurements are taken, the interface surface area facing a chamber is preferably less than 0.02 mm$^2$. In general, the interface containing the channels should have a design which minimizes the total access resistance to less than 20% of the theoretical (calculated) minimal convergence resistance. The total access resistance is the sum of the resistance contributed by the electrode/electrolyte interface, salt bridges, and the medium in the channel. The resistance of the medium in the channel includes the bulk resistance, the convergence resistance at each end of the channel, and the intra-channel resistance.

In addition, measurements can be temporally related to the interface, such as when a measurement is taken at a pre-determined time or range of times before or after each monomer passes into or out of the channel.

As an alternative to voltage, a nucleic acid polymerase or exonuclease can be provided in one of the chambers to draw the nucleic acid polymer through the channel as discussed below.

This invention offers advantages in nucleotide sequencing, e.g., reduced number of sequencing steps, higher speed of sequencing, and increased length of the polymer to be sequenced. The speed of the method and the size of the polymers it can sequence are particular advantages of the invention. The linear polymer may be very large, and this advantage will be especially useful in reducing template preparation time, sequencing errors and analysis time currently needed to piece together small overlapping fragments of a large gene or stretch of polymer.

Other features and advantages of the invention will be apparent from the following description of the preferred embodiments thereof, and from the claims.

BRIEF DESCRIPTION OF THE DRAWINGS

FIG. 6A illustrates the current blockages when polycytidylic oligonucleotides traverse a channel. FIG. 6B illustrates the current blockages when polyadenylic oligonucleotides traverse the channel. FIG. 6C illustrates the current blockages when polycytidylic and polyadenylic oligonucleotides traverse a channel.

DETAILED DESCRIPTION

As summarized above, we have determined a new method for rapidly analyzing polymers such as DNA and RNA. We illustrate the invention with two primary embodiments. In one embodiment, the method involves measurements of ionic current modulation as the monomers (e.g., nucleotides) of a linear polymer (e.g., nucleic acid molecule) pass through or across a channel in an artificial membrane. During polymer passage through or across the channel, ionic currents are reduced in a manner that reflects the properties of the polymer (length, concentration of polymers in solution, etc.) and the identities of the monomers. In the second embodiment, an immiscible interface is created between two immiscible liquids, and, as above, polymer passage through the interface results in monomer interactions with the interface which are sufficient to identify characteristics of the polymer and/or the identity of the monomers.

The description of the invention will be primarily concerned with sequencing nucleic acids, but this is not intended to be limiting. It is feasible to size and sequence polymers other than nucleic acids by the method of the invention, including linear protein molecules which include monomers of amino acids. Other linear arrays of monomers, including chemicals (e.g., biochemicals such as polysaccharides), may also be sequenced and characterized by size.

I. Polymer Analysis Using Conductance Changes Across an Interface

Figure 1:
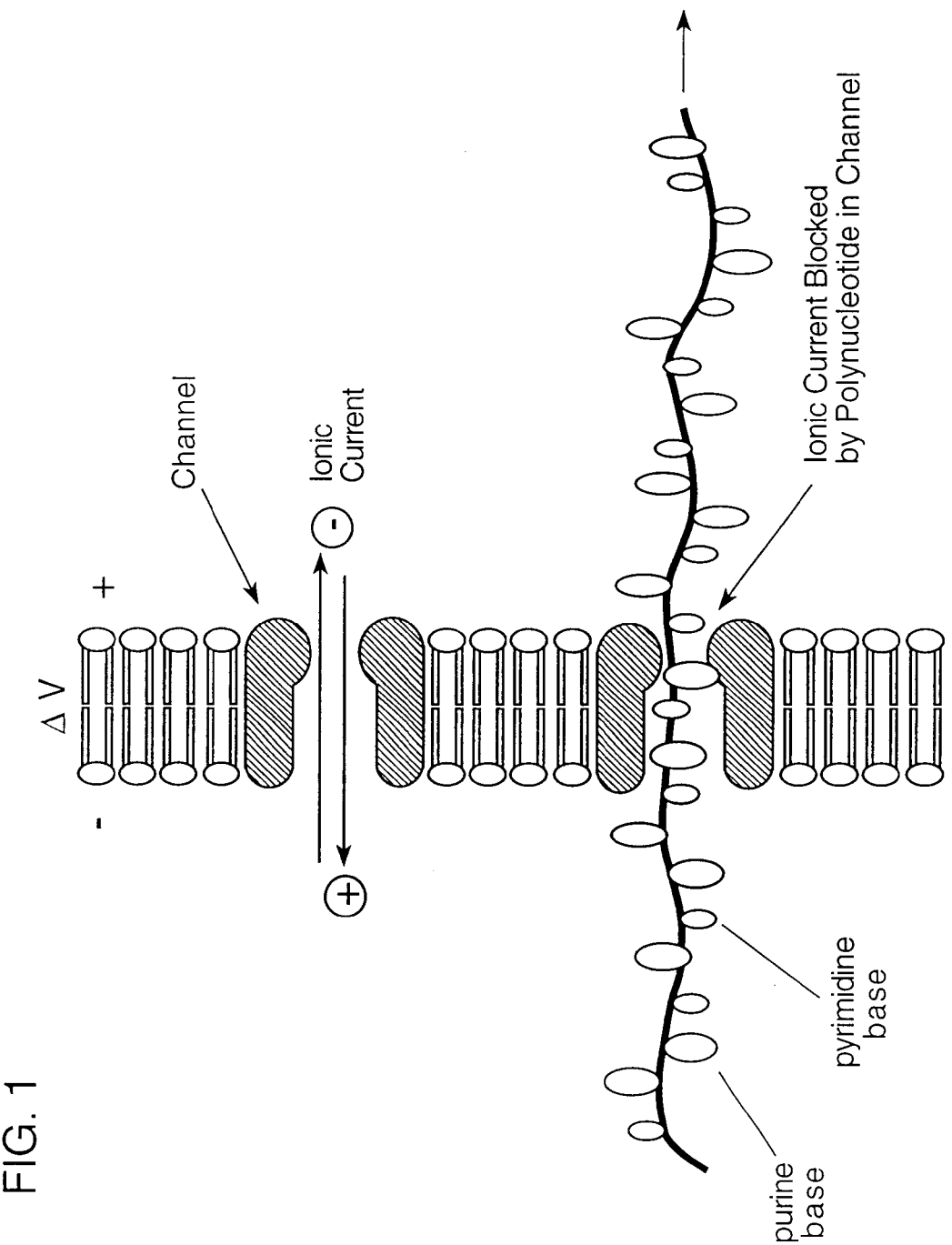
FIG. 1 is a schematic representation of an embodiment of DNA characterization by the method of the invention. The unobstructed ionic current (illustrated for the channel at the top of the diagram), is reduced as a polymeric molecule begins its traversal through the pore (illustrated for the channel at the bottom of the diagram).
Figure 2:
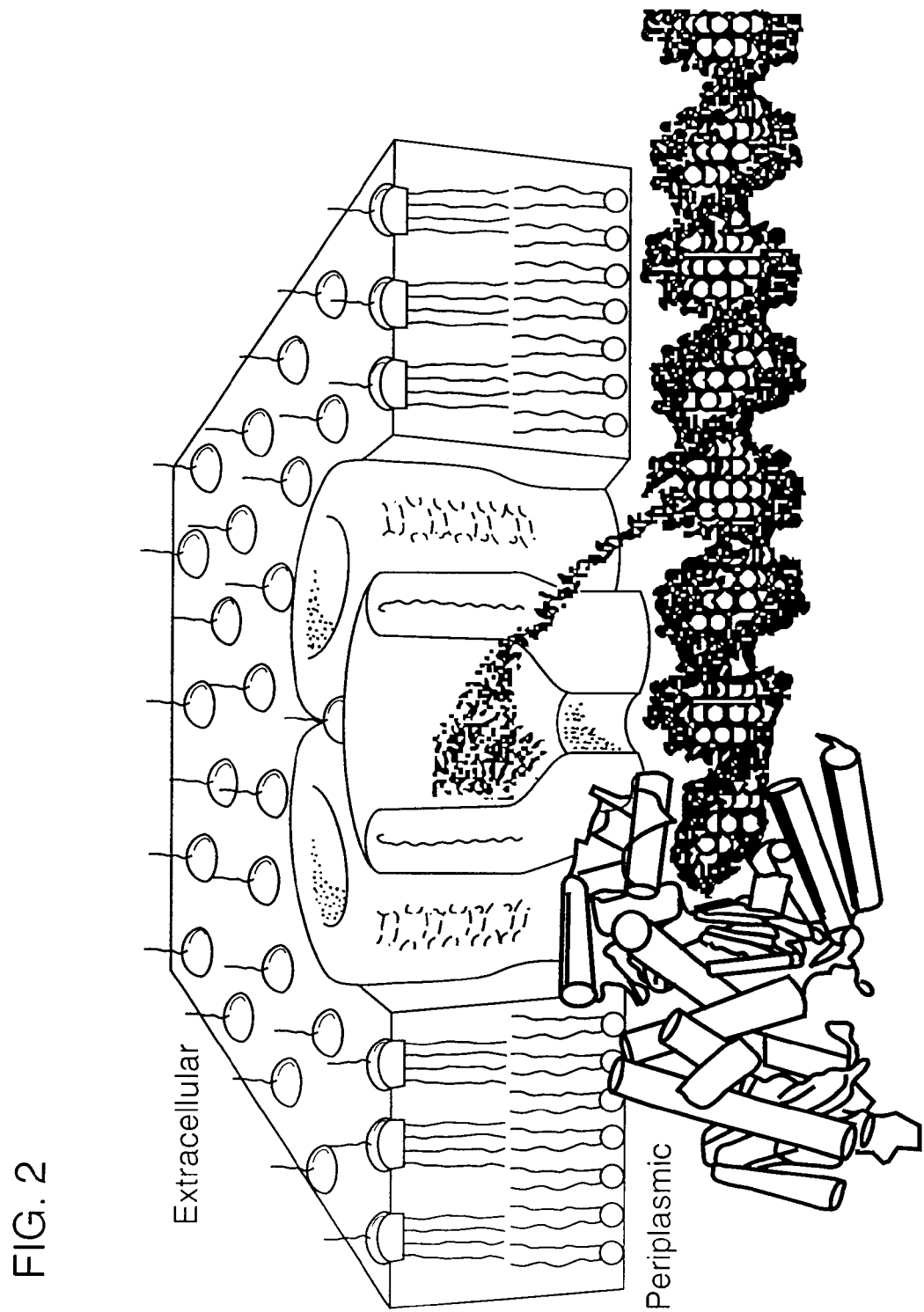
FIG. 2 is a schematic representation of an implementation of DNA sequencing by the method of the invention. In this embodiment, the polymer is drawn across the opening of the channel, but is not drawn through the channel. The channel, e.g., a porin, is inserted in the phospholipid bilayer. A polymerase domain is fused by its N-terminus to the C-terminus of one of the porin monomers (the porin C-termini are on the periplasmic side of the membrane in both *Rhodobacter capsulatus* and LamB porins) Fusions on the other side of the membrane can also be made. Malto-oligosaccharides can bind and block current from either side. The polymerase is shown just prior to binding to the promoter. A non-glycosylated base is shown near a pore opening, while a penta-glycosylated cytosine is shown 10 bp away. The polymerase structure represented is that of DNA polymerase I (taken from Ollis et al., 1985, *Nature*, 313:762–66), and the general porin model is from Jap (1989, *J. Mol. Biol.*, 205:407–19).
Figure 3:
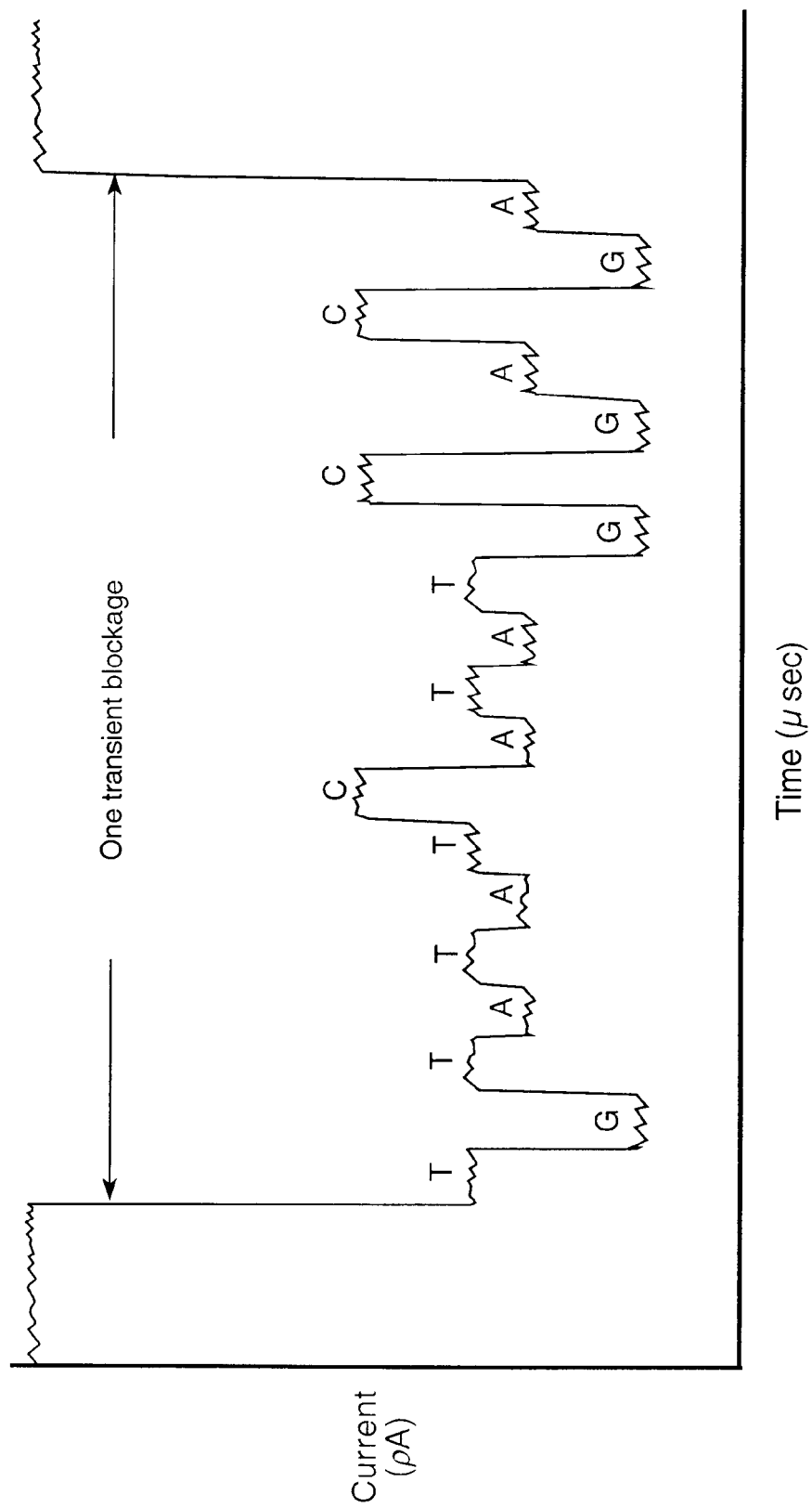
FIG. 3 is a schematic representation of DNA sequencing results by the method of the invention. The schematic depicts, at very high resolution, one of the longer transient blockages such as can be seen in FIG. 4. The monomeric units of DNA (bases G, A, T, and C) interfere differentially with the flow of ions through the pore, resulting in discrete conductance levels that are characteristic of each base. The order of appearance of the conductance levels sequentially identifies the monomers of the DNA.

Sensitive single channel recording techniques (i.e., the patch clamp technique) can be used in the invention, as a rapid, high-resolution approach allowing differentiation of nucleotide bases of single DNA molecules, and thus a fast and efficient DNA sequencing technique or a method to determine polymer size or concentration (FIGS. 1 and 2). We will describe methods to orient DNA to a pore molecule in two general configurations (see FIGS. 1 and 2) and record conductance changes across the pore (FIG. 3). One method is to use a pore molecule such as the receptor for bacteriophage lambda (LamB) or α-hemolysin, and to record the process of DNA injection or traversal through the channel pore when that channel has been isolated on a membrane patch or inserted into a synthetic lipid bilayer (FIG. 1). Another method is to fuse a DNA polymerase molecule to a pore molecule and allow the polymerase to move DNA over the pore's opening while recording the conductance across the pore (FIG. 2). A third method is to use a polymerase on the trans side of the membrane/pore divider to pull a single stranded nucleic acid through the pore from the cis side (making it double stranded) while recording conductance changes. A fourth method is to establish a voltage gradient across a membrane containing a channel (e.g., α-hemolysin) through which a single stranded or double stranded DNA is electrophoresed.

The apparatus used for this embodiment includes 1) an ion-conducting pore or channel, perhaps modified to include a linked or fused polymerizing agent, 2) the reagents necessary to construct and produce a linear polymer to be characterized, or the polymerized molecule itself, and 3) an amplifier and recording mechanism to detect changes in conductance of ions across the pore as the polymer traverses its opening.

A variety of electronic devices are available which are sensitive enough to perform the measurements used in the invention, and computer acquisition rates and storage capabilities are adequate for the rapid pace of sequence data accumulation.

A. Characteristics Identified by the Methods

1) Size/Length of Molecules

The size or length of a polymer can be determined by measuring its residence time in the pore or channel, e.g., by measuring duration of transient blockade of current. The relationship between this time period and the length of the polymer can be described by a reproducible mathematical function which depends on the experimental condition used. The function is likely a linear function for a given type of polymer (e.g., DNA, RNA, polypeptide), but if it is described by another function (e.g., sigmoidal or exponential), accurate size estimates may be made by first preparing a standard curve using known sizes of like linear molecules.

2) Identity of Residues/Monomers

The chemical composition of individual monomers is sufficiently variant to cause characteristic changes in channel conductance as each monomer traverses the pore due to physical configuration, size/volume, charge, interactions with the medium, etc. For example, our experimental data suggest that polyc RNA reduces conductance more than does polyA RNA, indicating a measurable physical difference between pyrimidines and purines that is one basis of nucleotide identification in this invention.

The nucleotide bases of DNA will influence pore conductance during traversal, but if the single channel recording techniques are not sensitive enough to detect differences between normal bases in DNA, it is practical to supplement the system's specificity by using modified bases. The modifications should be asymmetrical (on only one strand of double stranded template), to distinguish otherwise symmetrical base pairs.

Modified bases are readily available. These include: 1) methylated bases (lambda can package and inject DNA with or without methylated A's and C's), 2) highly modified bases found in the DNA of several bacteriophage (e.g. T4, SP15), many of which involve glycosylations coupled with other changes (Warren, 1980, *Ann. Rev. Microbiol.*, 34:137–58), and 3) the modified nucleotide triphosphates that can be incorporated by DNA polymerase (e.g. biotinylated, digoxigenated, and fluorescently tagged triphosphates).

In order to identify the monomers, conditions should be appropriate to avoid secondary structure in the polymer to be sequenced (e.g., nucleic acids); if necessary, this can be achieved by using a recording solution which is denaturing. Using single stranded DNA, single channel recordings can be made in up to 40% formamide and at temperatures as high as 45° C. using e.g., the α-hemolysin toxin protein in a lipid bilayer. These conditions are not intended to exclude use of any other denaturing conditions. One skilled in the art of electrophysiology will readily be able to determine suitable conditions by 1) observing incorporation into the bilayer of functional channels or pores, and 2) observing transient blockades of conductance uninterrupted by long-lived blockades caused by polymers becoming stuck in the channel because of secondary structure. Denaturing conditions are not always necessary for the polymerase-based methods or for double stranded DNA methods of the invention. They may not be necessary for single stranded methods either, if the pore itself is able to cause denaturation, or if the secondary structure does not interfere.

3) Concentration of Polymers in Solutions

Concentration of polymers can be rapidly and accurately assessed by using relatively low resolution recording conditions and analyzing the number of conductance blockade events in a given unit of time. This relationship should be linear and proportional (the greater the concentration of polymers, the more frequent the current blockage events), and a standardized curve can be prepared using known concentrations of polymer.

B. Principles and Techniques

1) Recording Techniques

The conductance monitoring methods of the invention rely on an established technique, single-channel recording, which detects the activity of molecules that form channels in biological membranes. When a voltage potential difference is established across a bilayer containing an open pore molecule, a steady current of ions flows through the pore from one side of the bilayer to the other. The nucleotide bases of a DNA molecule, for example, passing through or over the opening of a channel protein, disrupt the flow of ions through the pore in a predictable way. Fluctuations in the pore's conductance caused by this interference can be detected and recorded by conventional single-channel recording techniques. Under appropriate conditions, with modified nucleotides if necessary, the conductance of a pore can change to unique states in response to the specific bases in DNA.

This flux of ions can be detected, and the magnitude of the current describes the conductance state of the pore. Multiple conductance states of a channel can be measured in a single recording as is well known in the art. By recording the fluctuations in conductance of the maltoporin (LamB) pore, for example, when DNA is passed through it by phage lambda injection or over its opening by the action of a polymerase fused to the surface of the LamB protein, we estimate that a sequencing rate of 100–1000 bases/sec/pore can be achieved.

The monitoring of single ion channel conductance is an inexpensive, viable method that has been successful for the last two decades and is in very wide spread current use. It directly connects movements of single ions or channel proteins to digital computers via amplifiers and analog to digital (A to D, A/D) converters. Single channel events taking place in the range of a few microseconds can be detected and recorded (Hamill et al., 1981, *Pfluegers Arch. Eur. J. Physiol.*, 391:85–100). This level of time resolution ranges from just sufficient to orders of magnitude greater than the level we need, since the time frame for movement of nucleotide bases relative to the pore for the sequencing method is in the range of microseconds to milliseconds. The level of time resolution required depends on the voltage gradient or the enzyme turnover number if the polymer is moved by an enzyme. Other factors controlling the level of time resolution include medium viscosity, temperature, etc.

The characteristics and conductance properties of any pore molecule that can be purified can be studied in detail using art-known methods (Sigworth et al., supra; Heinemann et al., 1988, *Biophys. J.*, 54:757–64; Wonderlin et al., 1990, *Biophys. J.*, 58:289–97). These optimized methods are ideal for our polymer sequencing application. For example, in the pipette bilayer technique, an artificial bilayer containing at least one pore protein is attached to the tip of a patch-clamp pipette by applying the pipette to a preformed bilayer reconstituted with the purified pore protein in advance. Due to the very narrow aperture diameter of the patch pipette tip (2 microns), the background noise for this technique is significantly reduced, and the limit for detectable current interruptions is about 10 microseconds (Sigworth et al., supra; Heinemann et al., 1990, *Biophvs. J.*, 57:499–514). Purified channel protein can be inserted in a known orientation into preformed lipid bilayers by standard vesicle fusion techniques (Schindler, 1980, *FEBS Letters*, 122:77–79), or any other means known in the art, and high resolution recordings are made. The membrane surface away from the pipette is easily accessible while recording. This is important for the subsequent recordings that involve added DNA. The pore can be introduced into the solution within the patch pipette rather than into the bath solution.

An optimized planar lipid bilayer method has recently been introduced for high resolution recordings in purified systems (Wonderlin et al., supra). In this method, bilayers are formed over very small diameter apertures (10–50 microns) in plastic. This technique has the advantage of allowing access to both sides of the bilayer, and involves a slightly larger bilayer target for reconstitution with the pore protein. This optimized bilayer technique is an alternative to the pipette bilayer technique.

Instrumentation is needed which can apply a variable range of voltages from about +400 Mv to –400 mV across the channel/membrane, assuming that the trans compartment is established to be 0 mV; a very low-noise amplifier and current injector, analog to digital (A/D) converter, data acquisition software, and electronic storage medium (e.g., computer disk, magnetic tape). Equipment meeting these criteria is readily available, such as from Axon Instruments, Foster City, Calif. (e.g., Axopatch 200B system; pClamp 7.0 software).

Preferred methods of large scale DNA sequencing involve translating from base pairs to electronic signals as directly and as quickly as possible in a way that is compatible with high levels of parallelism, miniaturization and manufacture. The method should allow long stretches (even stretches over 40 kbp) to be read so that errors associated with assembly and repetitive sequence can be minimized. The method should also allow automatic loading of (possibly non-redundant) fresh sequences.

2) Channels and Pores Useful in the Invention

Any channel protein which has the characteristics useful in the invention (e.g., pore sized up to about 9 nm) may be employed. Pore sizes across which polymers can be drawn may be quite small and do not necessarily differ for different polymers. Pore sizes through which a polymer is drawn will be e.g., approximately 0.5–2.0 nm for single stranded DNA; 1.0–3.0 nm for double stranded DNA; and 1.0–4.0 nm for polypeptides. These values are not absolute, however, and other pore sizes might be equally functional for the polymer types mentioned above.

Examples of bacterial pore-forming proteins which can be used in the invention include Gramicidin (e.g., Gramicidin A from *Bacillus brevis*; available from Fluka, Ronkonkoma, N.Y.); LamB (maltoporin), OmpF, OmpC, or PhoE from *Escherichia coli*, *Shigella*, and other Enterobacteriaceae, alpha-hemolysin (from *S. aureus*), Tsx, the F-pilus, lambda exonuclease, and mitochondrial porin (VDAC). This list is not intended to be limiting.

A modified voltage-gated channel can also be used in the invention, as long as it does not inactivate quickly, e.g., in less than about 500 msec (whether naturally or following modification to remove inactivation) and has physical parameters suitable for e.g., polymerase attachment (recombinant fusion proteins) or has a pore diameter suitable for polymer passage. Methods to alter inactivation characteristics of voltage gated channels are well known in the art (see e.g., Patton, et al., *Proc. Natl. Acad. Sci. USA*, 89:10905–09 (1992); West, et al., *Proc. Natl. Acad. Sci. USA*, 89:10910–14 (1992); Auld, et al., *Proc. Natl. Acad. Sci. USA*, 87:323–27 (1990); Lopez, et al., *Neuron*, 7:327–36 (1991); Hoshi, et al., *Neuron*, 7:547–56 (1991); Hoshi, et al., *Science*, 250:533–38 (1990), all hereby incorporated by reference).

Appropriately sized physical or chemical pores may be induced in a water-impermeable barrier (solid or membranous) up to a diameter of about 9 nm, which should be large enough to accommodate most polymers (either through the pore or across its opening). Any methods and materials known in the art may be used to form pores, including track etching and the use of porous membrane templates which can be used to produce pores of the desired material (e.g., scanning-tunneling microscope or atomic force microscope related methods).

Chemical channels or pores can be formed in a lipid bilayer using chemicals (or peptides) such as Nystatin, as is well known in the art of whole-cell patch clamping ("perforated patch" technique); and peptide channels such as Alamethicin.

Template-dependent nucleic acid polymerases and free nucleotides can be used as a motor to draw the nucleic acids through the channel. For example, the DNA to be sequenced is placed in one chamber; RNA polymerases, nucleotides, and optionally primers are placed in the other chamber. As the 3' end of the DNA passes through the channel (via a voltage pulse or diffusion, for example), the RNA polymerase captures and begins polymerization. If the polymerase is affixed to the chamber or is physically blocked from completely passing through the channel, the polymerase can act as a rachet to draw the DNA through the channel.

Similarly, lambda exonuclease, which is itself shaped as a pore with a dimension similar to α-hemolysin, can operate as a motor, controlling the movement of the nucleic acid polymer through the channel. The exonuclease has the added benefit of allowing access to one strand of a double stranded polymer. As the double stranded polymer passes through the pore, the exonuclease grabs onto the 5' single-stranded overhang of a first strand (via endonuclease digestion or breathing of the double stranded DNA ends) and sequentially cleaves the complementary second strand at its 3' end. During the sequential cleavage, the exonuclease progresses 5' to 3' down the first strand, pulling the double stranded DNA through the channel at a controlled rate. Thus, the exonuclease can operate as a pore as well as a motor for drawing the nucleic acid polymer through the channel.

To produce pores linked with polymerase or exonuclease, synthetic/recombinant DNA coding for a fusion protein can be transcribed and translated, then inserted into an artificial membrane in vitro. For example, the C-terminus of *E. coli* DNA polymerase I (and by homology, T7 DNA polymerase) is very close to the surface of the major groove of the newly synthesized DNA. If the C-terminus of a polymerase is fused to the N-terminus of a pore forming protein such as colicin E1 and the colicin is inserted into an artificial membrane, one opening of the colicin pore should face the DNA's major groove and one should face the opposite side of the lipid bilayer. For example, the colicin molecule can be modified to achieve a pH optimum compatible with the polymerase as in Shiver et al. (*J. Biol. Chem.*, 262:14273–14281 1987, hereby incorporated by reference). Both pore and polymerase domains can be modified to contain cysteine replacements at points such that disulfide bridges form to stabilize a geometry that forces the pore opening closer to the major groove surface and steadies the polymer as it passes the pore opening. The loops of the pore domain at this surface can be systematically modified to maximize sensitivity to changes in the DNA sequence.

C. General Considerations for Conductance Based Measurements

1) Electrical/Channel Optimization

The conductance of a pore at any given time is determined by its resistance to ions passing through the pore (pore resistance) and by the resistance to ions entering or leaving the pore (access resistance). For a pore's conductance to be altered in discrete steps, changes in one or both of these resistance factors will occur by unit values. The base pairs of a DNA molecule represent discrete units that are distinct from each other along the phosphate backbone. As long as the orientation of DNA to the pore remains relatively constant, and the membrane potential does not change, as each base pair passes by (or through) the pore, it is likely to interfere with a reproducible number of ions. Modifications made to the individual bases would influence the magnitude of this effect.

To resolve stretches of repeating identical bases accurately, and to minimize reading errors in general, it may be useful for the pore to register a distinct (probably higher) level of conductance in between the bases. This can take place naturally in the pore-polymerase system with helix rotation during polymerization, or in the phage system between entry of base pairs into the pore, or when the regions in between base pairs pass by a rate limiting site for ion flux inside the pore. Modified bases used to distinguish nucleotide identities may also contribute significantly to this issue, because they should magnify the conductance effect of the bases relative to the effect of regions in between the bases. With single strand passage through a pore, charged phosphates may punctuate the passage of each base by brief, higher conductance states. Also, if the rate of movement is constant, then punctuation between bases may not be required to resolve stretches of repeating identical bases.

Altered conductance states have been described for many channels, including some LamB mutants (Dargent et al., 1988, supra). A mutant may be a valuable alternative to a wild type channel protein if its fluctuation to a given state is sensitive to nucleotide bases in DNA. Alternative systems can also be developed from other channel proteins that are known to have multiple single channel conductance states. Examples of these are the alamethicin channel, which under certain conditions fluctuates through at least 20 discrete states (Taylor et al., 1991, *Biophys. J.*, 59:873–79), and the OmpF porin, which shows gating of its individual monomers giving rise to four discrete states (Lakey et al., 1989, *Eur. J. Biochem.*, 186:303–308).

Since channel events can be resolved in the microsecond range with the high resolution recording techniques available, the limiting issue for sensitivity with the techniques of our invention is the amplitude of the current change between bases. Resolution limits for detectable current are in the 0.2 pA range (1 pA=$6.24 \times 10^6$ ions/sec). Each base affecting pore current by at least this magnitude is detected as a separate base. It is the function of modified bases to affect current amplitude for specific bases if the bases by themselves are poorly distinguishable.

One skilled in the art will recognize that there are many possible configurations of the sequencing method described herein. For instance, lipid composition of the bilayer may include any combination of non-polar (and polar) components which is compatible with pore or channel protein incorporation. Any configuration of recording apparatus may be used (e.g., bilayer across aperture, micropipette patches, intra-vesicular recording) so long as its limit of signal detection is below about 0.5 pA, or in a range appropriate to detect monomeric signals of the polymer being evaluated. If polymeric size determination is all that is desired, the resolution of the recording apparatus may be much lower.

A Nernst potential difference, following the equation $$E_{ion} = (RT/zF)\log_e([ion]_o/[ion]_i)$$

where $E_{ion}$ is the solvent ion (e.g., potassium ion) equilibrium potential across the membrane, R is the gas constant, T is the absolute temperature, z is the valency of the ion, F is Faraday's constant, $[ion]_o$ is the outside and $[ion]_i$ is the inside ionic concentration (or trans and cis sides of the bilayer, respectively), can be established across the bilayer to force polymers across the pore without supplying an external potential difference across the membrane. The membrane potential can be varied ionically to produce more or less of a differential or "push." The recording and amplifying apparatus is capable of reversing the gradient electrically to clear blockages of pores caused by secondary structure or cross-alignment of charged polymers.

2) Optimization of Methods

In an operating system of the invention, one can demonstrate that the number of transient blockades observed is quantitatively related to the number of polymer molecules that move through the channel from the cis to the trans compartment. By sampling the trans compartment solution after observing one to several hundred transient blockades and using quantitative, competitive PCR assays (e.g., as in Piatak et al., 1993, *BioTechniques*, 14:70–79) it is possible to measure the number of molecules that have traversed the channel. Procedures similar to those used in competitive PCR can be used to include an internal control that will distinguish between DNA that has moved through the channel and contaminating or aerosol DNA.

Further steps to optimize the method may include:

1. Slowing the passage of polynucleotides so that individual nucleotides can be sensed. Since the blockade durations we observed are in the millisecond range, each nucleotide in a one or two thousand monomer-long polynucleotide occupies the channel for just a few microseconds. To measure effects of individual nucleotides on the conductance, substantially reducing the velocity may offer substantial improvement. Approaches to accomplish this include: (a) increasing the viscosity of the medium, (b) establishing the lower limit of applied potential that will move polynucleotides into the channel (c) use of high processivity polymerase in the trans compartment to "pull" DNA through the pore in place of voltage gradients. Using enzymes to pull the DNA through the pore may also solve another potential problem (see 3, below).

2. Making a channel in which an individual nucleotide modulates current amplitude. While α-toxin may give rise to distinguishable current amplitudes when different monopolynucleotides pass through the channel, 4–5 nucleotides in the strand necessarily occupy the length of its approximately 50 Å long channel at any given time. Ionic current flow may therefore reflect the sum of the nucleotide effects, making it difficult to distinguish monomers. To determine current modulation attributable to individual monomers, one may use channels containing a limiting aperture that is much shorter than the full length of the overall channel (Weiss et al., supra). For example, one can modify α-hemolysin by standard molecular biological techniques such that portions of the pore leading to and away from the constriction are widened.

3. Enhancing movement of DNA in one direction. If a DNA molecule is being pulled through a channel by a voltage gradient, the probability of its moving backward against the gradient will be given by $$e^{-(\text{energy to move against the voltage gradient}/kT)}$$

where kT is energy associated with thermal fluctuations. For example, using reasonable assumptions for the effective charge density of the DNA polyelectrolyte in buffer (Manning, 1969, *J. Chem. Phys.*, 51:924–33), at room temperature the probability of thermal energy moving the DNA molecule backward-10 Å against a 100 mV voltage gradient $\approx e^{-4}$ or about one in fifty. Should this problem exist, some kind of ratchet mechanism, possibly a polymerase or other DNA binding protein, may be useful in the trans chamber to prevent backward movements of the DNA.

3) Advantages of Single Channel Sequencing

The length of continuous DNA sequence obtainable from the methods described herein will only be limited in certain embodiments (e.g., by the packaging limit of phage lambda heads (~50 kb) or by the size of the template containing polymerase promoter sequences). Other embodiments (e.g., voltage gradients) have no such limitation and should even make it possible to sequence DNA directly from tissue samples, since the technique is not limited to cloned DNA. Having large contiguous sequence as primary input data will substantially reduce the complexity of sequence assembly, particularly in the case of repetitive DNA. There are other applications if consistent conductance behaviors can be correlated with particular properties of given molecules (i.e. shape).

D. Specific Methods and Examples of Current Based Characterization

The following specific examples of current based polymer characterization are presented to illustrate, not limit the invention.

1) The LamB Pore

Maltoporin (LamB) is an outer membrane protein from *E. coli* that functions as a passive diffusion pore (porin) for small molecules and as a specific transport pore for passage of maltose and maltodextrins (Szmelcman et al., 1975, *J. Bacteriol.*, 124:112–18). It is also the receptor for bacteriophage lambda (Randall-Hazelbauer and Schwartz, 1973, *J. Bacteriol.* 116:1436–1446). Three identical copies of the LamB gene product assemble to form the native pore. Each subunit (MW ~48,000) is composed of predominantly beta-structure and is a pore in itself, though it is thought that the three pores fuse into one at the periplasmic side of the membrane (Lepault et al., 1988, *EMBO, J.*, 7:261–68).

A protein folding model for LamB is available that predicts which portions of the mature protein reside on the external and periplasmic surfaces of the membrane (Charbit et al., 1991, *J. Bacteriol.*, 173:262–75). Permissive sites in the protein have been mapped to several extramembranous loops that tolerate the insertion of foreign polypeptides without significantly disrupting pore properties (Boulain et al., 1986, *Mol. Gen. Genet.*, 205:339–48; Charbit et al., 1986, *EMBO J.*, 5:3029–37; Charbit et al., 1991, supra). The LamB protein has been crystallized and a high resolution structure derived (3.1 Å) (Schirmer et al., 1995, *Science*, 267:512–514).

The pore properties of wild type LamB and a few mutant proteins have been studied at low resolution in planar lipid bilayer single channel recordings (Benz et al., 1986, *J. Bacteriol.*, 165:978–86; Benz et al., 1987, *J. Membrane Biol.*, 100:21–29; Dargent et al., 1987, *FEBS Letters*, 220:136–42; Dargent et al., 1988, *J. Mol. Biol.*, 201:497–506). The pore has a very stable conductance of 150 pS in 1M NaCl, and shows selectivity for maltose and maltodextrins. These molecules effectively block conductance of the pore. One LamB mutant (Tyr$^{163}$→Asp) exhibits distinct sublevels of conductance (30 pS each).

The LamB pore is extremely stable, and high time resolution recordings can be made for use in this invention. The time resolution of channel conductance measurements with the conventional planar lipid bilayer technique is limited because of the background noise associated with the high electrical capacitance of bilayers formed on large diameter apertures (100–200 microns), but smaller apertures or insulated glass microelectrodes can improve the resolution of LamB channel recordings. Preferably, improved LamB conductance recordings will use the pipette bilayer technique (Sigworth et al., supra).

EXAMPLE 1

Conductance Measurements of Lambda DNA Injection

Bacteriophage lambda injects its DNA through the LamB pore at a rate of about 1000 bp/sec (Novick et al., 1988, *Biochemistry*, 27:7919–24). Lambda will inject its DNA into liposomes reconstituted with purified *E. coli* LamB protein. Alcohol or chloroform may be useful in this system (Randall-Hazelbauer and Schwartz, 1973, supra), but if the solvents disrupt current recordings, one can use either the LamB protein from a closely related species, e.g., Shigella sonnei 3070, which allows spontaneous lambda DNA injection into liposomes (Schwartz et al., 1975, *J. Virol.*, 15:679–85; Roessner et al., 1983, *J. Biol. Chem.*, 258:643–48), or a hybrid protein containing portions of LamB from both species, which behaves similarly (Roessner et al., 1987, *J. Mol. Biol.*, 195:963–66).

The conductance of single LamB pores is monitored during the addition of phage to the medium bathing the bilayer. An initial change in conductance upon phage binding will be followed by a drop in conductance as DNA enters the pore. Any sustained conductance fluctuations that follow are indicative of base pairs passing through the pore during injection. The fluctuations should be in the millisecond range, and the period of fluctuation will generally last for about 60 sec (the time required for injection). The conductance should then go up again to a level even higher than the original pre-phage state, since post-injection phage/porin complexes have been observed to allow molecules larger than the normal LamB exclusion limit to pass through (Roessner et al., 1986, *J. Biol. Chem.*, 261:386–90).

Asymmetrically modified DNA produced by annealing modified and unmodified complementary strands or by custom primed DNA synthesis, can be ligated to lambda vector DNA and packaged in vitro. Modified DNA that is packaged efficiently and can be injected into bacterial cells will be appropriate for the LamB sequencing system.

EXAMPLE 2

Conductance Measurements of Pore-Polymerase Complexes

Alternatively, the pore makes use of a polymerase molecule to pass DNA over the pore's opening one base pair at a time. Nucleotide bases of DNA will affect ion flux through the pore as they are passed over it by the polymerase, and the corresponding conductance fluctuations can be detected by high resolution single-channel recording techniques. The polymerase is held in position at the pore's surface as part of a fusion protein with the pore (see FIG. 2).

Fusion proteins are constructed (e.g., LamB and T7 RNA polymerase) such that both pore and polymerase are functional. The permissive sites in LamB (or any other desired pore protein) that can accommodate insertion of polypeptide sequences without significantly disrupting pore properties are targeted for these fusions. Accommodation of an entire active protein has been demonstrated for *E. coli* membrane proteins (Boyd et al., 1987, *Proc. Natl. Acad. Sci. USA*, 84:8525–29; Ehrmann et al., 1990, *Proc. Natl. Acad. Sci. USA*, 87:7574–78; both hereby incorporated by reference). At least some of the LamB permissive sites (12 have been described) will support insertion of the polymerase. T7 RNA polymerase is best fused to the C-terminal end of LamB, since the polymerase is known to function in protein fusions with this orientation (Ostrander et al., 1990, *J. Bacteriol.*, 116:1436–46; hereby incorporated by reference).

Fusion constructions can be screened for LamB function on MacConkey agar plates containing maltooligosaccharides. This screen is sensitive enough to detect a range of partial LamB functions. Fusion proteins with even partially functional pores should have high conductance states in bilayer experiments prior to DNA addition. Purified pore polymerase fusion proteins can be assayed for T7 RNA polymerase activity or used directly to reconstitute liposomes in preparation for channel recordings.

FIG. 2 shows a schematic representation of a possible pore-polymerase fusion complex with template DNA. The orientation of the base pairs to the pore opening is likely to alternate through several potential angles, due to the polymerase having some freedom of movement. For this reason, nucleotide base modifications that take into account the specific properties of the pore will be helpful to observe consistent conductance effects. For instance, the selectivity of LamB for maltose and maltooligosaccharides is a promising area of nucleotide modification for this system, particularly since these molecules have a dramatic effect on LamB conductance in vitro (Benz et al., 1986, supra; Benz et al., 1987, supra; Dargent et al., 1987, supra).

The affinity of maltooligosaccharides for LamB increases in proportion to the number of glucose residues attached (up to five) (Benz et al., 1987, supra), thus, nucleotides attached to maltose or maltooligosaccharides are likely to block the pore more effectively than unsubstituted nucleotides. Furthermore, the number of glucose molecules attached to a substituted nucleotide may significantly influence the effect it has on LamB conductance. By substituting specific bases with modified nucleotides linked to a given number of oligosaccharide units, it should be possible to relate those substituted bases with predictable conductance states of the pore.

EXAMPLE 3

Testing Pore Fusions

The above system can be tested with a short oligonucleotide containing the T7 RNA polymerase promoter attached to phage T4 DNA that is asymmetrically modified at C residues with oligoglucose chains. The oligonucleotide template is made with the modified bases on the displaced strand, because T7 RNA polymerase has been shown to function when nucleotide analogs are present on this strand (Nath et al., 1991, *Carcinogenesis*, 12:973–76). The conductance of pore-polymerase complexes is monitored while adding this template and ribonucleotide triphosphates (NTPs) to the system. By adding the NTPs sequentially, one can sample the polymerase at four positions relative to the start site. This provides conductance information pertaining to the modified cytosine closest to the promoter at several distances from (and orientations to) the pore. By adding all four NTPs, the effects of each modified base as it passes the pore can be sampled during RNA synthesis.

The conductance profiles for this modified fragment are compared with control fragments containing no modifications to correlate given conductance shifts with the modified nucleotides. Uniform lengths for the oligoglucosyl moieties on given bases can be obtained by HPLC purifying the modified dNTPs. Additional pore-polymerase geometries and defined glucose chain lengths on modified bases are also within the scope of the invention.

EXAMPLE 4

Recording from Shigella LamB

We have made recordings from Shigella LamB channels. We modified the pipette bilayer technique of Sigworth et al. (supra) by adding purified Shigella LamB to the solution inside the patch pipette, rather than to the bath solution. This modification has provided more consistent pore activity. We estimate the single channel conductance of this pore to be 120 pS (recording in bilateral 0.83M KCl, +25 mV). This is similar to the conductance of LamB from *E. coli* (Benz et al., 1986, supra; Dargent et al., 1987, supra; Benz et al., 1987, supra; Dargent et al., 1988, supra). Our equipment and technique have the potential for recording at very high resolution.

We tested the effect of a maltooligosaccharide mixture on the conductance of Shigella LamB, since maltooligosaccharides are known to inhibit the conductance of *E. coli* LamB in planar lipid bilayer experiments (Dargent et al., 1987, supra; Benz et al., 1987, supra) and can be used for nucleotide modifications. Our recordings show that the conductance of Shigella LamB molecules is inhibited by the addition of maltooligosaccharides to the bath. In the same recordings, we have shown that the conductance of these pores increases as the concentration of maltooligosaccharide in the bath is reduced. This reversible inhibition of conductance by maltooligosaccharides is similar to that observed for the *E. coli* protein (Dargent et al., 1987, supra).

In our experiments testing the effects of lambda DNA injection on the conductance of LamB pores, the Shigella protein was chosen because lambda will spontaneously inject its DNA in vitro when bound to this receptor, as opposed to the E. coli receptor, which requires the presence of organic compounds (ethanol or chloroform) for lambda injection. LamB conductance was altered when lambda injected its DNA through the pore, and the conductance changes were detectable during a patch-clamp recording. We have obtained several classes of response when lambda is added to the bath during patch-clamp recordings of Shigella LamB, ranging from no response at all to nearly complete inhibition of conductance, to rapidly fluctuating conductance levels. We observed that under the bath conditions used for patch-clamp recording, our preparation of Shigella LamB is routinely capable on inducing lambda DNA injection in vitro.

Multiple pores in the patch membrane at one time make it difficult to interpret the lambda response, and it is important to obtain single pores in the patch membrane.

Advantages of Using Phage Lambda to Orient DNA to Pore
1) The system is simple to set up.
2) Lambda injection is efficient and fast.
3) Lambda vectors are used extensively to construct genomic and cDNA libraries, thus there is a tremendous resource of potential sequence information readily available for direct application of this technique.
4) The average insert size for cosmid libraries is about 45 kb; this sets the average "read" size of contiguous DNA sequence. While this is less than the potential read size for a functional pore-polymerase complex (see below), it is still about 100 times the average read size for most conventional sequencing. Ion flux can take place through phage receptor pores that contain phage DNA. T5 provides an alterative phage system (as do T3, T4 and P1, all of which have efficient in vitro packaging systems).

The membrane spanning length of LamB pores is estimated to be 30 Å (Benz et al., 1987, supra). Thus, at any given time during DNA injection, 8–9 base pairs of DNA are present in the pore. For the effects of single base pairs on pore current to be more easily measurable, it is preferable to have a region of the pore that is rate limiting for ion flux past one or two base pairs. Such a region may take the form of an "eyelet" structure as seen in the R. capsulatus porin (Weiss et al., supra), where steric interactions are limiting, or, depending on the exact amino acids involved, hydration, electrostatic, as well as steric interactions may produce a rate limiting site. Alternatively, since it is likely that the bacteriophage tail fiber widens the LamB pore upon phage attachment, and it is possible that the phage DNA passes through the fiber during injection, the bottle neck for ion flow may be at some position along the inside of the tail fiber.

Advantages of the Pore-polymerase System for Orienting DNA to the Pore
1) This system offers some flexibility in orienting DNA to the pore's opening, and thus provides the mechanism to optimize this orientation.
2) The average size of contiguous sequence obtainable by this technique is very large; it is limited by the processivity of T7 RNA polymerase since there is no obvious template size restriction. T7 RNA polymerase is highly processive in vitro (Golomb et al., Proc. Natl. Acad. Sci. USA, 71:760–64; Niles et al., supra; Oakley et al., 1975, Biochemistry, 14:4684–91).
3) The rate of sequencing with this system is also very high, limited only by the rate of polymerase activity when fused to the pore. The rate of T7 RNA polymerase is ~300 bases/sec (Martin et al., 1987, Biochemistry, 26:2690–96). This provides an estimate of the sequencing rate for this system.
4) In principal, any source of DNA can be used as template for this system, provided it contains the T7 RNA polymerase promoter. This includes high molecular weight DNA from tissue samples which is ligated to a T7 promoter oligonucleotide.

The fusion proteins constructed must have at least partial pore function to ensure a high single-channel conductance, so that there will be "room" for lower conductance states when DNA is added.

The polymerase portion of the fusion can be considered an external protein domain of the pore. This polymerase domain must demonstrate activity when the complex is inserted into bilayers. T7 RNA polymerase is known to function when fused to the C-terminus of other proteins (Ostrander et al., supra). Thus, this orientation to LamB should be productive, provided the C-terminal amino acids of LamB remain intact (Boulain et al., supra). The permissive sites of LamB are particularly attractive for polymerase-insertion, since most of these sites map to regions predicted to form extramembranous loops (Charbit et al, 1991, supra), and several proteins have been shown to function when inserted at such sites in other membrane proteins (Boyd et al., supra; Ehrmann et al., 1990, supra). Our cloning scheme is designed to allow variation in the length of peptide linkers at either end of the polymerase insertion site.

The LamB protein forms a trimer, so expressing the pore-polymerase construct in cells that otherwise lack LamB protein will result in a pore with three polymerases. Such complexes may be unstable or nonfunctional. This problem can be avoided by producing heterotrimers between normal LamB monomers and pore-polymerase monomers. Functional LamB heterotrimers between normal and mutant forms have been observed (Ferenci et al., 1989, J. Bacteriol., 171:855–61; hereby incorporated by reference).

The orientation of the polymerase to the pore's opening must be such that during polymerization, nucleotide bases are positioned close enough to affect ion flux through the pore. The mouth of the pore is small compared to the polymerase or DNA, thus, polymerase activity at the pore's surface will affect ion access. Some configurations, however, may be better suited for sequencing, in that they may provide more consistent conductance readings.

Several insertion target sites for LamB have been described, although random insertion is an option with our screening approach. It is also possible to express domains of the polymerase at different sites in LamB, such that they fold together on the pore's surface into an optimal configuration. Alternatively, by using two polymerase molecules per trimer, the template might be anchored over the pore in a more optimal position. Information provided by the progressing crystallographic investigations of these two proteins (Sousa et al., 1989, Proteins: Struct. Funct. Genet., 5:266–70; Stauffer et al., 1990, J. Mol. Biol., 211:297–99) may be useful to help design the geometry of the fusion to suit the needs of the project. We are not limited to these particular proteins, however, since in principle any channel molecule and any processive nucleic acid translocation molecule could potentially suffice. An example is the conjugation process in E. coli, where genome-sized (single-stranded) DNA is transported through the F-pilus at a rate of about 780 bp/sec (Rees et al., 1989, J. Bacteriol., 171:3152–57; Harrington et al., 1990, J. Bacteriol., 172:7263–64). This process can be monitored in situ with the patch-clamp technique.

The oligoglucosyl chains attached to modified bases are expected to have considerable rotational freedom. If each LamB monomer has a binding site for maltooligosaccharides, which is the present model (Ferenci et al., supra), then conductance readings from one base pair may be obscured by the side chains from adjacent base pairs interacting with other pores in the trimer. This problem can be overcome by using heterotrimers containing LamB mutant monomers that have low maltose binding affinity complexed with wild type monomers (or a hyperbinding mutant) in a ratio of 2:1. It has been shown that low maltose affinity monomers do not prevent maltodextrin transport when present in heterotrimers (Ferenci et al., supra).

2) The Alpha-Hemolysin Pore Forming Protein

Discussion and examples of the invention using the bacterial pore-forming protein α-hemolysin toxin (α-toxin or α-hemolysin) are below. This system operates as shown in FIG. 1; nucleic acid polymers are threaded through the α-toxin pore as shown, and the monomeric charges and physical obstruction alter ionic conductance through the pore. Because the purine and pyrimidine bases in the polynucleotide have differing molecular sizes and chemical properties, a specific ionic current will flow as each nucleotide enters and passes through the channel, thus electro-sensing the monomer sequence in the linear polymer.

EXAMPLE 5

Bilayer Recordings from α-Hemolysin

For these experiments, the bacterial pore-forming protein from *S. aureus*, α-hemolysin, forms a heptamer that spontaneously embeds in lipid bilayers, producing a current conducting channel. α-hemolysin forms a robust channel which has the appropriate diameter to admit a single stranded DNA polymer. Furthermore, it can remain open for indefinite time periods when subjected to a continuous voltage gradient. Diphytanoyl phosphatidylcholine was used to form lipid bilayer membranes across 0.2 mm holes in a Teflon film separating two compartments containing buffer solution of the following composition: 1 M NaCl, 10 mM Tris, pH 7.4 (Montal et al., 1972, *PNAS*, 69:3561). In initial, multi-channel experiments, α-hemolysin was added to the cis side of the bilayer and approximately 10 channels were allowed to incorporate into the bilayer before excess α-hemolysin was removed. Voltage applied across the bilayer was then varied from 0 mV to 140 mV. Under the buffer conditions used, the channels were continuously open before addition of polynucleotide. After addition of poly A to the cis chamber, the channels began to exhibit transient blockades at potentials greater than 100 mV. Similar effects were seen with poly C and poly U polymer additions. Significantly, the blockades only occurred when the voltage was applied in the direction expected to produce electrophoretic movements of a poly-anion like RNA from the cis to the trans side of the channel, i.e., only when the trans side was positive.

Figure 4:
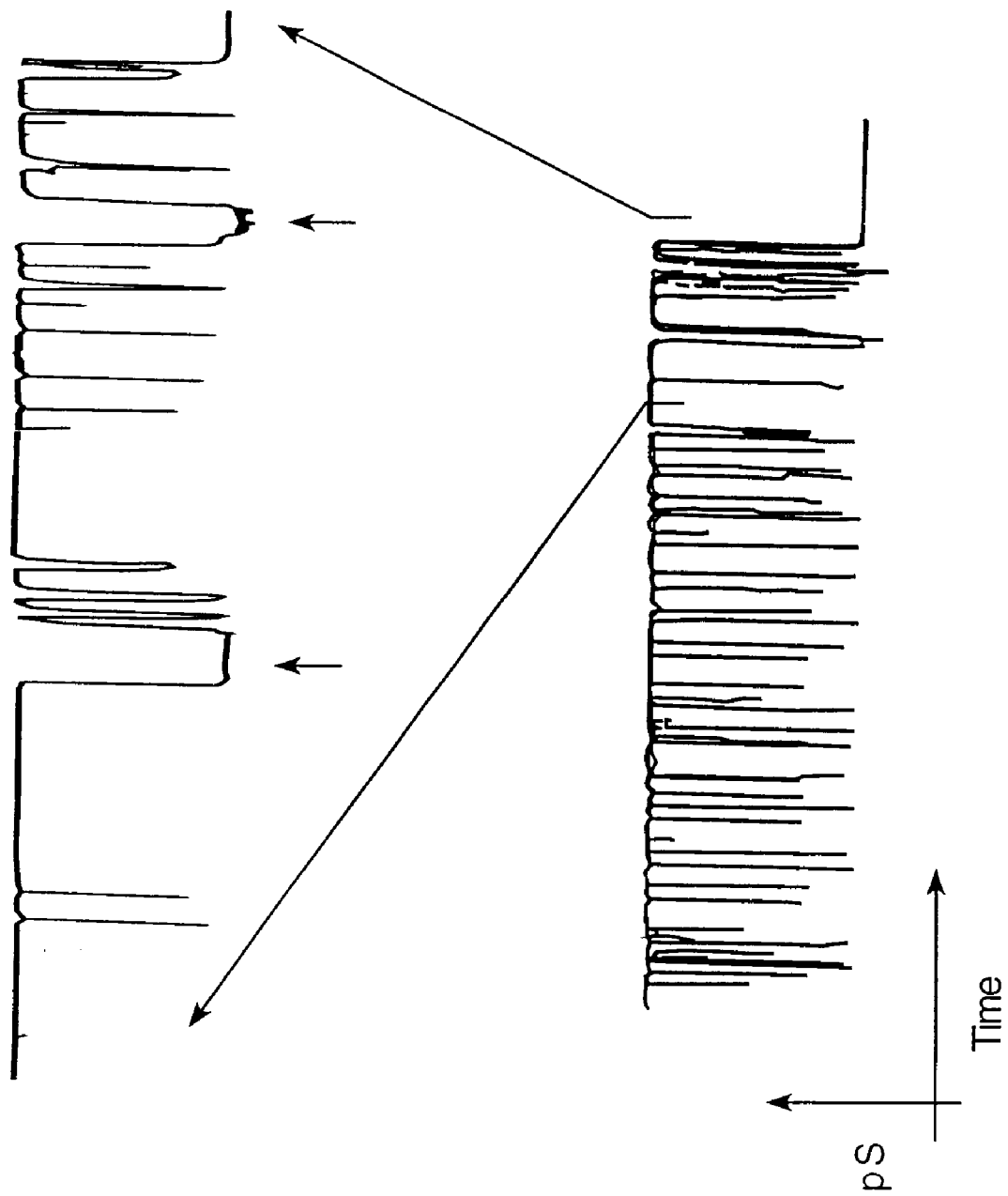
FIG. 4 is a recording of the effect of polyadenylic acid (poly A) on the conductance of a single α-hemolysin channel in a lipid bilayer between two aqueous compartments containing 1 M NaCl, 10 Mm Tris, Ph 7.4. Before addition of RNA, the conductance of the channel was around 850 Ps. The cis compartment, to which poly A is added, is –120 mV with respect to the trans compartment. After adding poly A to the cis compartment, the conductance of the α-hemolysin channel begins to exhibit transient blockages (conductance decreases to about 100 Ps) as individual poly A molecules are drawn across the channel from the cis to the trans compartment. When viewed at higher resolution (expanded time scale, at top), the duration of each transient blockage is seen to vary between less than 1 msec up to 10 msec. Arrows point to two of the longer duration blockages. See FIGS. 5A and 5B for histograms of blockage duration.

Further experiments with single channels demonstrated many well-resolved individual channel blockades in the presence of poly A, poly C, or poly U molecules (for example, see FIG. 4). Qualitatively, the number of transient blockades was proportional to the concentration of polynucleotide. Typical current blockades exhibited 85–95% reductions of current amplitude and lasted up to several milliseconds. Because the polynucleotide preparations used in these experiments contain a range of molecular weights, we could not quantitatively relate blockade duration to polynucleotide length. But qualitatively, average blockade duration was greater when using solutions containing longer RNA polymers (MW 140 kb –1700 kb) than when using solutions containing shorter polymers (MW 77 kb –160 kb). Occasionally, long-lived blockades of several seconds or more were observed. These often cleared spontaneously, but could always be cleared by briefly reversing the voltage polarity. Again, there was virtually no effect on the magnitude of channel conductance when the trans side was negative. To verify that the polynucleotides were producing the long-lived blockades, RNAse was added to the RNA in the cis chamber to gradually hydrolyze it. When RNAse was added to polyuridylic oligonucleotides in the cis chamber while transient blockades were being observed, the duration of the transient blockades, but not their amplitude, gradually decreased over a period of several minutes, eventually becoming too short to be detectable.

From these experiments, it is apparent that polynucleotides are not simply binding to the channel and causing it to partially close, because if that were true, the current blockades would not depend on the polarity of the voltage gradient. Our interpretation is that ionic current through a channel can be modulated by passage of single polymer strands. This interpretation is supported by the fact that ribonuclease decreases the duration but not the amplitude of the current blockades. It is also consistent with our observation that circular single-stranded molecules appear to produce virtually no blockades and that double-stranded molecules with single stranded ends produce only indefinitely long-lived blockades.

EXAMPLE 6

Relationship Between Polymer Length and Channel Blockade Duration

Figure 5A:
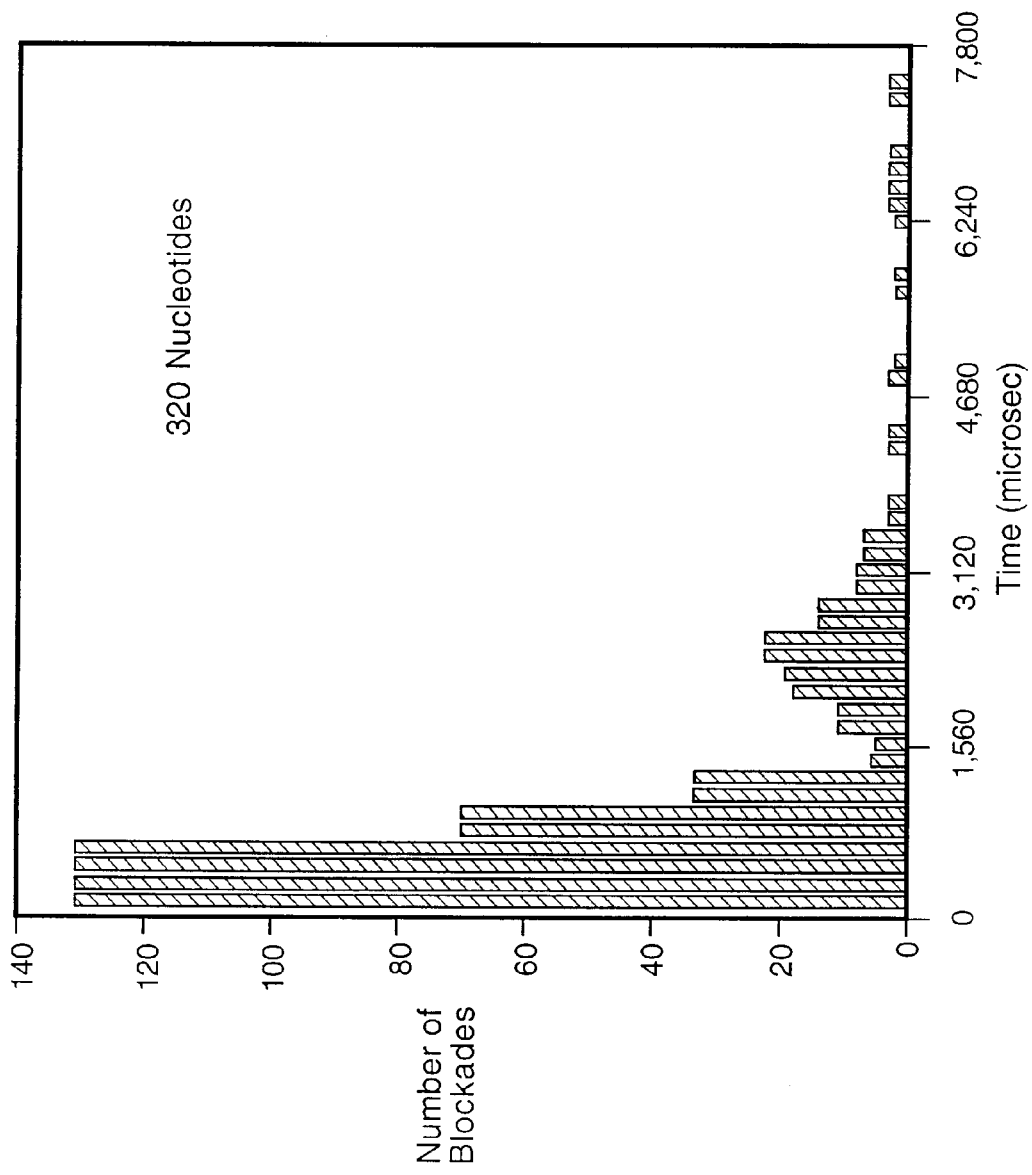
FIGS. 5A and 5B are comparisons of blockage duration with purified RNA fragments of 320 nt (FIG. 5A) and 1100 nt (FIG. 5B) lengths. The absolute number of blockades plotted in the two histograms are not comparable because they have not been normalized to take into account the different lengths of time over which the data in the two graphs were collected.
Figure 5B:
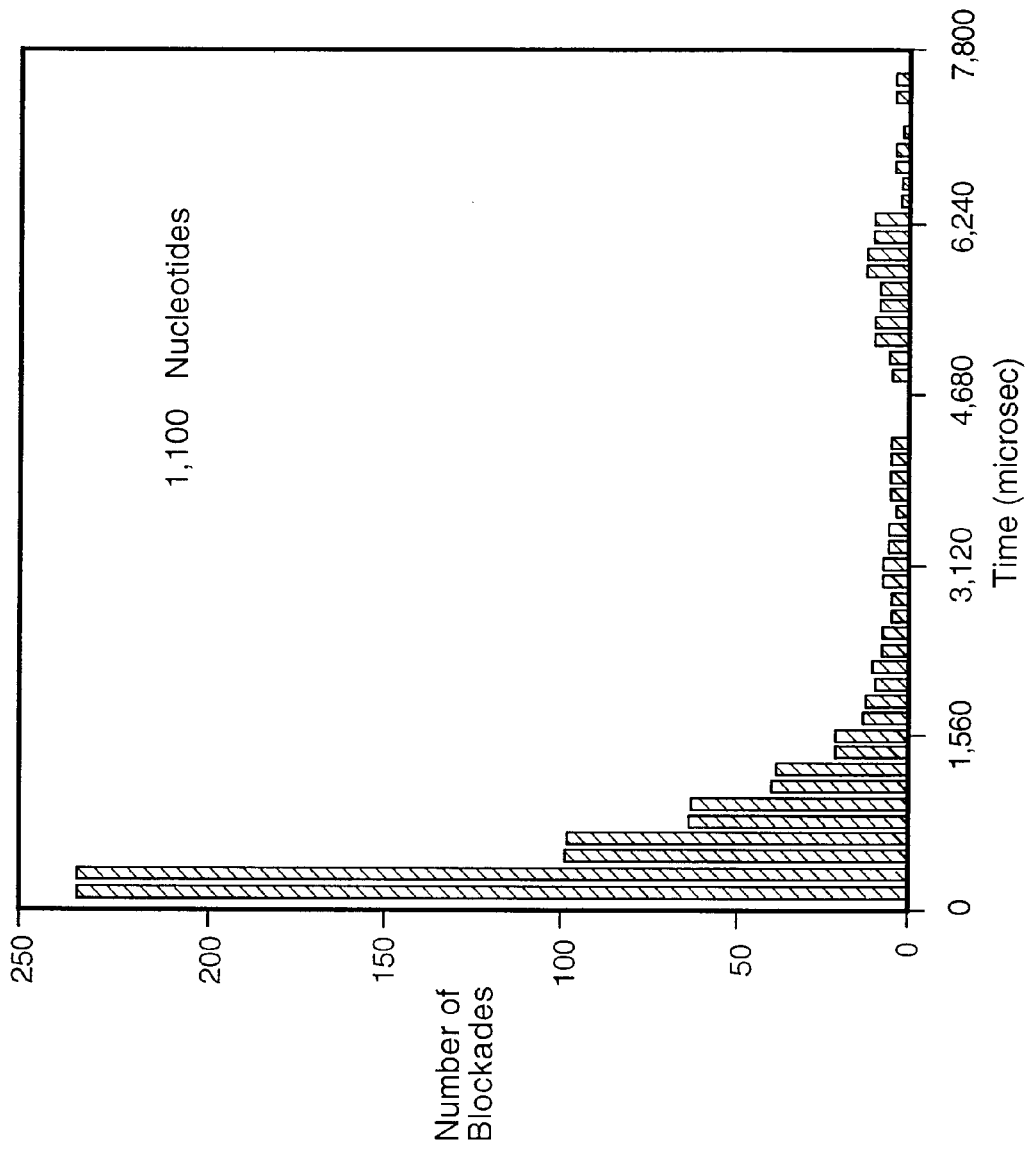

To determine the relation between chain length and duration of the current blockade, we used samples of synthetic short (~320 nt) and long (~1,100 nt) polyuridylic oligonucleotides that we size-selected by gel electrophoresis. These experiments have been repeated, with several independently purified polyuridylic acid samples which gave consistent results. Using polymers whose chain length centered around 320 nt, about 35% of the recorded current blockades had lifetimes of around 2.1 msec at 120 mV (FIG. 5A), and around 1.7 msec at 140 mV (data not shown), with the remaining signals having short lifetimes of <1 msec. We presume that the short duration blockades represent polymers that interact with the channel (e.g., loops of polymer that come to lie on the channel aperture, without fully entering and traversing the channel). We attribute the clear peak of blockades centered around 2.1 msec or 1.7 msec (depending on applied voltage) to polymers that have traversed the channel, because: 1) Based on the consistency of the peak position from run to run, the shift in peak position from 2.1 msec at 120 mV to 1.7 msec at 140 mv is statistically significant and hard to explain by any model other than a polymer being threaded through the channel; 2) When RNA that had not been size-selected (e.g., RNA containing the full range of polymer lengths from 250 nt to 1600 nt) was used, we detected the corresponding full range of blockade durations rather than durations that exhibited a "narrow" peak (as seen in FIGS. 5A and 5B); and 3) Experiments with the ca 1,100 nt polymers have shown a peak centered around 5.8–6 msec at 140 mV (FIG. 5B). If one assumes a linear relationship between polymer size and blockade duration, it can be seen that 1100 nt/320 nt=3.4 and that 3.4×1.7 msec=5.8 msec, lending credibility to the accuracy of the methods of the invention for measuring polymer length by measuring signal duration.

EXAMPLE 7

Sequencing Two Different Oligonucleotide Homopolymers

To determine if a mixture of two different oligonucleotide homopolymers in one chamber of the methods of the invention can be sequenced, α-hemolysin pores were generated in lipid bilayers as described in Example 5 above and in Kasianowicz et al., 1996, *Proc. Natl. Acad. Sci. USA*, 93:13770–13773.

Figure 6A:
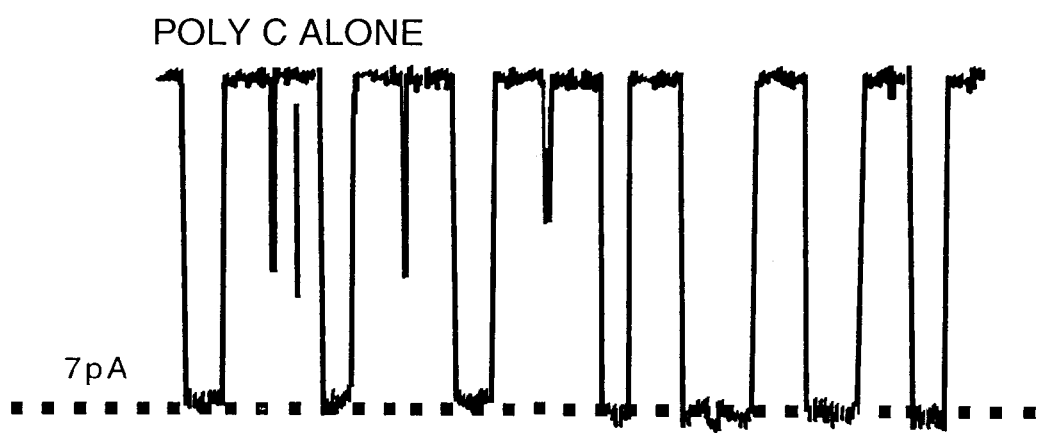
FIGS. 6A, 6B, and 6C are plots of current measurements versus time according to a method of the invention.
Figure 6B:
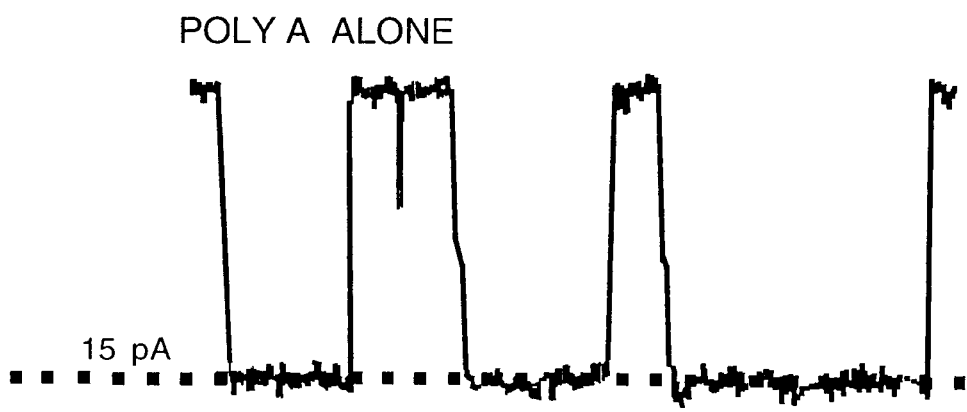
Figure 6C:
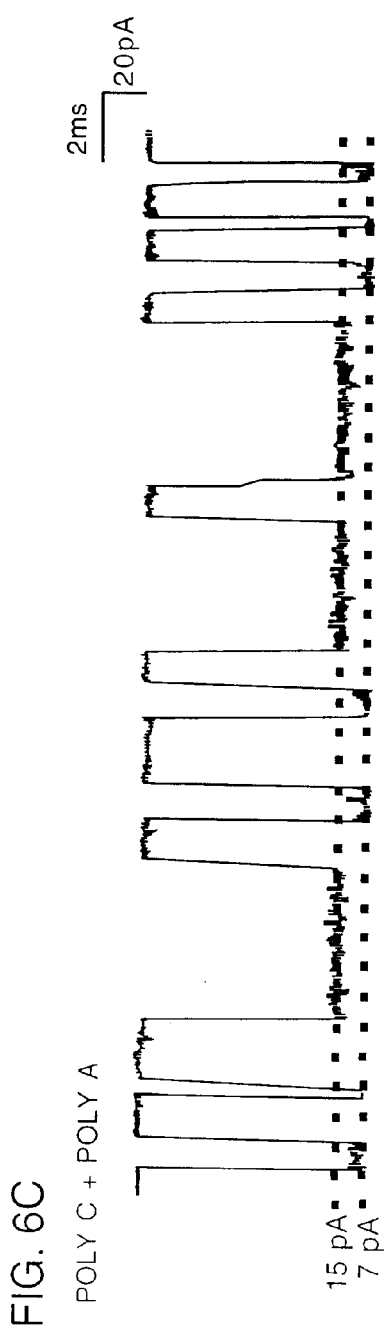

As a control, the current blockages caused by polycytidylic and polyadenylic oligonucleotides of 200 nucleotide average length were measured. FIG. 6A shows that the polycytidylic oligonucleotides decreased ionic current flow to a consistent 7 pA. In contrast, FIG. 6B shows that the polyadenylic oligonucleotides decreased ionic current to a consistent 15 pA. When the polycytidylic and polyadenylic oligonucleotides were introduced into the same chamber and ionic current flows measured (FIG. 6C), the two types of oligonucleotides were distinguishable. FIG. 6C shows that, while polycytidylic oligonucleotide traversal through the pore lead to current decreases to 7 pA as expected, the polyadenylic oligonucleotide traversal through the pore led to current decreases to 15 pA.

EXAMPLE 8

Sequencing an Oligonucleotide Heteropolymer

Figure 7:
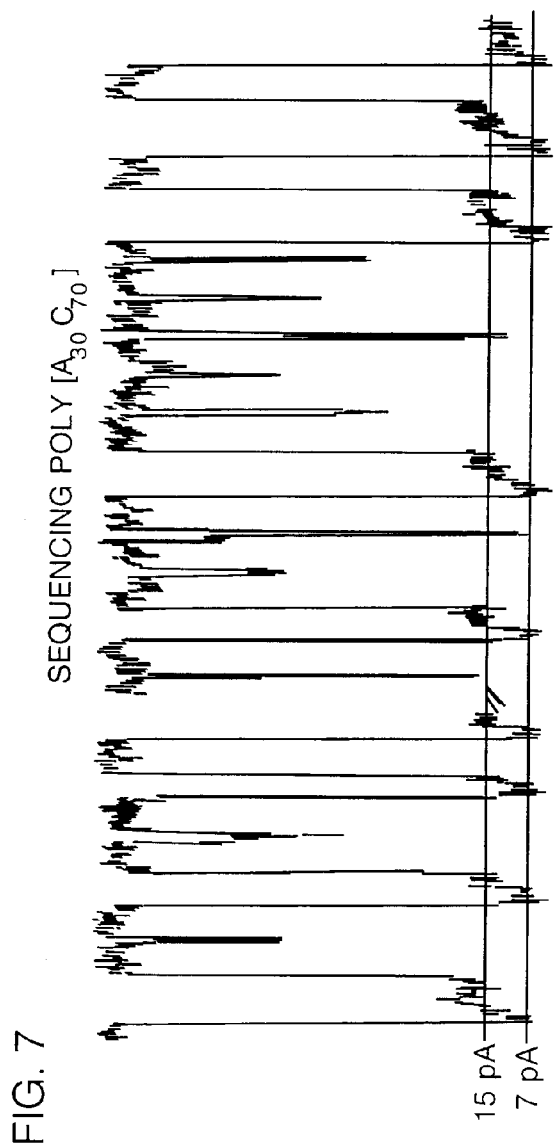
FIG. 7 is a plot of current measurements versus time according to a method of the invention, illustrating the current blockages when $polyA_{30}C_{70}$ oligonucleotides traverse a channel.

To determine if oligonucleotides containing different nucleotide monomers can be sequenced, α-hemolysin lipid bilayers were formed as described in Example 5 above and in Kasianowicz et al., 1996, *Proc. Natl. Acad. Sci. USA*, 93:13770–13773. Oligonucleotides having 30 adenine bases followed by 70 cytosine (5' to 3', polyA$_{30}$/C$_{70}$) bases were added to one side of the lipid bilayer. As indicated in the graph of FIG. 7, the different monomers in each oligonucleotide were distinguished by the consistent blockage of current down to 7 pA for cytosine immediately followed by a blockage of 15 pA for adenine. The oligonucleotides apparently traversed the channels 3' end first.

EXAMPLE 9

Detection of Polymer Hybridization

It was next determined whether the double-stranded or single-stranded regions of a nucleic acid could be determined by monitoring the passage of the nucleic acid through a pore. In the following experiment, the typical translocation blockade duration of a single stranded DNA composed of 60 nucleotides (SEQ ID NO:7), of which 50 were a continuous sequence of deoxyadenine (polydA$_{50}$) and 11 nucleotides attached to the end of the polydA$_{50}$. The 11 nucleotides are selected so as to form a hairpin at the end of the polydA$_{50}$ sequence (see box in the graph shown in FIG. 8). A completely single stranded polydA$_{60}$ polymer (SEQ ID NO:8) was used for comparison. The experimental system was built and the measurements were taken generally as described in Example 7, except as indicated below.

Figure 8:
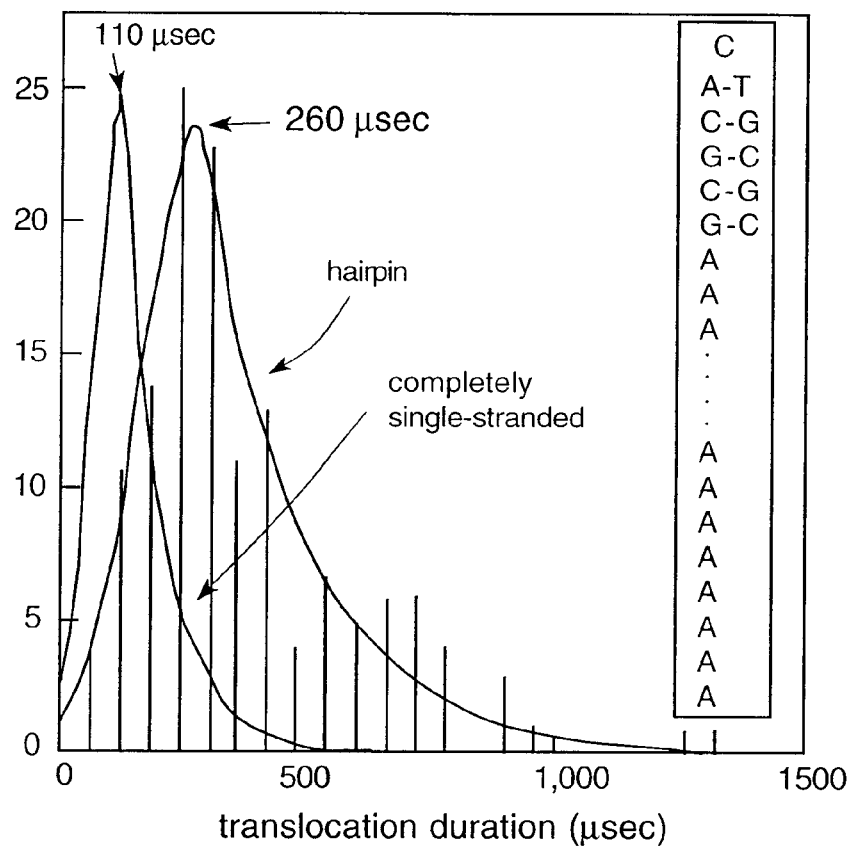
FIG. 8 is a histogram of the number of translocation events at different time points.

As shown in the box within the graph of FIG. 8, the hairpin sequence included 5 nucleotides that base-pair to form a double-stranded region. Graphed in FIG. 8 is the translocation duration histograms of a few hundred blockade events for the completely single-stranded polydA$_{60}$, and a partially single-stranded polymer with a "hairpin loop."

The peak corresponding to the polymer with the hairpin structure (260 μsec) had a value which was more than double that of the reference single stranded DNA (110 μsec). Note that both polymers were almost identical in length (61 bases and 60 bases). The extra 150 μsec delay in the translocation duration of the hairpin polymer may have been due to the melting of the double-stranded portion of the polymer containing the hairpin.

This result supported the proposition that double-stranded DNA can be melted using pores in an interface. Had the double-stranded hairpin not been melted during passage of the polymer, a blockade of indefinite length would have resulted because double-stranded DNA has too great a diameter to pass through the narrow pore in α-hemolysin (Kasianowicz et al., supra). The duration of the blockades created by passage of the polymer with a double-stranded region (the hairpin) was long enough to be clearly distinguished from blockades caused by passage of single stranded DNA, thereby allowing discrimination between single stranded and double stranded portions of a nucleic acid.

Figure 9:
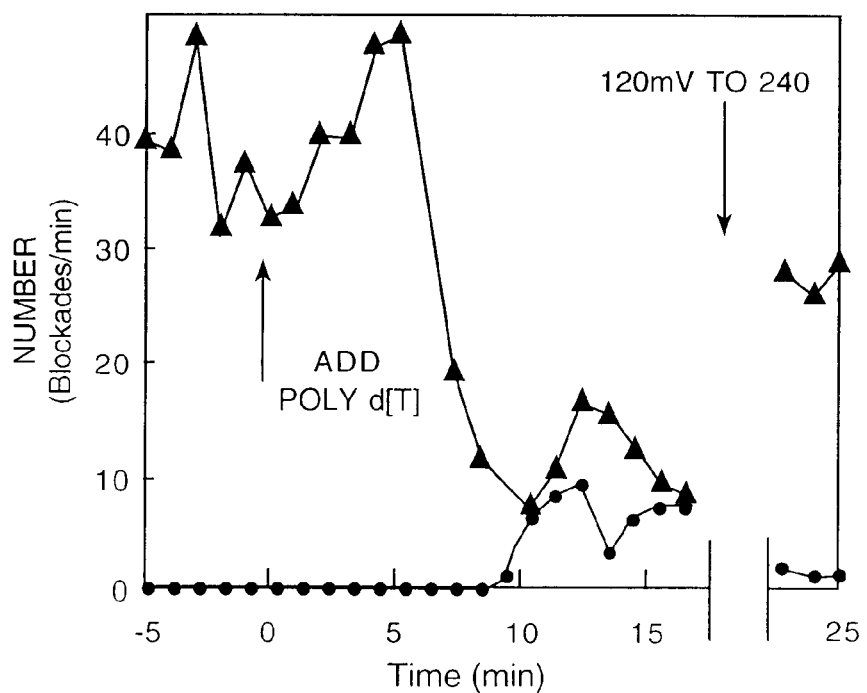
FIG. 9 is a graph of time versus the number of blockade events per minutes.

In another experiment, polymers of single-stranded DNA composed of 100 deoxyadenine nucleotides (polydA$_{100}$) were passed through an α-hemolysin channel in a lipid bilayer membrane using a voltage gradient of 120 mV. The number of DNA molecules traversing the channel was measured by recording and counting the number of blockades created by passing each polydA$_{100}$ molecule through the channel (FIG. 9). Next, polydT was added to the polyda molecules. The polydT would be expected to hybridize with polydA$_{100}$ to form primarily partially double-stranded, partially single-stranded DNA hybrids. It was therefore expected that a single-stranded end of the hybrid would be pulled into the channel, followed by a pause caused by the attempted entry of the double-stranded region of the hybrid into the pore. This pause was termed a "permablock," which is any blockade whose duration exceeds an arbitrarily selected duration. To remove permablocks, the applied voltage could be reversed to clear the channel. Such permablocks arose because the diameter of the double stranded portion of DNA (about 20 Angstroms) was too large to readily slip through the 15 Angstrom limiting aperture of the α-hemolysin channel used in this experiment.

For experiments such as the one immediately above that involve nucleic acids at least partially double-stranded, a "permabuster" device that measures the duration of a blockade and reverses the direction of the applied voltage gradient after an arbitrarily set time can be used. The device would then clear the channel of polymers until the next double-stranded region of polymer occupies the channel and causes the next permablock. A "permabust" is therefore a process for clearing the channel by reversing the direction of the applied voltage.

If the set time before the permabust routine is initiated is set at a low value (one that is lower than the minimum amount of time required for the double stranded portion of DNA to be melted as it traverses the channel), permablocks would have been seen only after the added polydT diffuses throughout the solution chamber and hybridizes with the polydA$_{100}$ that was already in the chamber (FIG. 9).

From the experiments in FIG. 9, permablocks were defined as blockades of greater than 500 msec. Permablocks were seen after adding polydT because at 120 mV the time for melting of DNA is significantly greater than the time required for the applied voltage gradient to pull unhybridized, single-stranded polydA through the channel.

When greater energy (240 mV) was used to pull the DNA across the membrane, blockade signals characteristic of DNA being pulled through the channels were again observed (FIG. 9). This was because the greater voltage gradient pulled the double-stranded region of DNA through the pore in less than the set time interval (500 msec) that initiated a permabust routine.

Figure 10A:
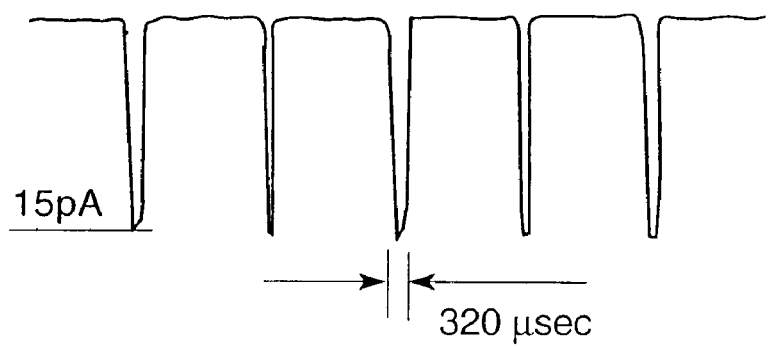
FIGS. 10A and 10B are current flow tracings through time.
Figure 10B:
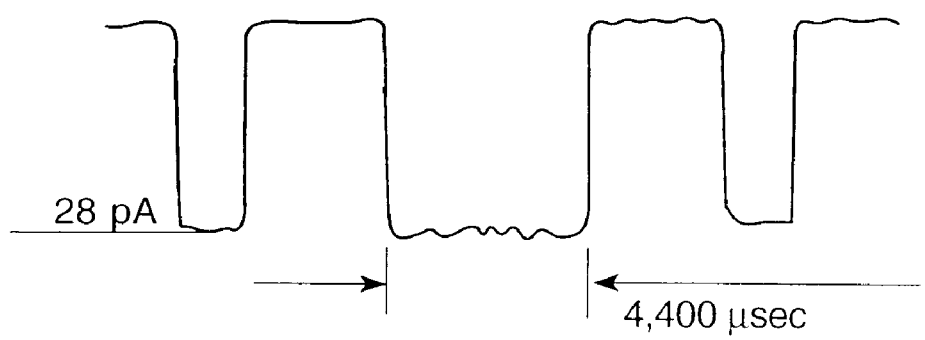

The current and blockades observed when single-stranded polyda and partially single-stranded, partially double-stranded polydA/polydT hybrids were pulled through the channel are shown in FIGS. 10A and 10B. Even at the higher voltage gradient of 240 mV, the hybridized DNA traversed the channel at a slower rate than the completely single-stranded DNA. The duration of one of the channel blockades was increased from 320 μsec to 4,400 μsec. It was also noted that, as a consequence of applying a greater voltage gradient across the membrane, the current that flows during the blockade is increased from 15 pA to 28 pA. Both the increased duration of the blockade (indicative of slower polymer traversal), as well as the greater current flow (the consequence of using a greater energy drop to drive the polymer) could contribute to greater precision in the measurement of current flow during channel occupancy by a traversing polymer.

In a separate experiment employing deoxyguanine and deoxycytosine nucleotide-containing DNA, similar permablocks and retarded passage of double-stranded DNA was seen.

The results as a whole then showed that DNA could be moved across the channel or pore in a pulsatile fashion by applying a rapidly pulsating voltage gradient that shifts between two states: (1) a small voltage gradient (e.g. 100 mV) that is capable of pulling single-strand regions of DNA into the pore and holding the DNA in the pore; and (2) a greater voltage gradient (e.g., 240 mV) that is believed to melt double-stranded regions of DNA, thus allowing the single strand of DNA that is in the pore to advance through the pore.

Recording both the blockade level (the current that flows through the channel during occupancy by a polymer) and the blockade duration (the time during which a channel exhibits occupancy as a single molecule traverses the channel), and then plotting the blocked current magnitude as a function of blockade duration, produce what was termed "event plots." Event plots were produced using the following polymers:

a) an analyte, a single stranded DNA polymer containing 100 nucleotides with sequence:

(SEQ ID NO:1)
5'-CTC ACC TAT CCT TCC ACT CAT TTT CCT TAA CCA

TTT CAT TCA CCC ATG TCA CTA TCA TTA TCT ACA

TCC ATT ACA TCA CTA CTC CTC ACA CTA CCA TAC

Figure 11A:
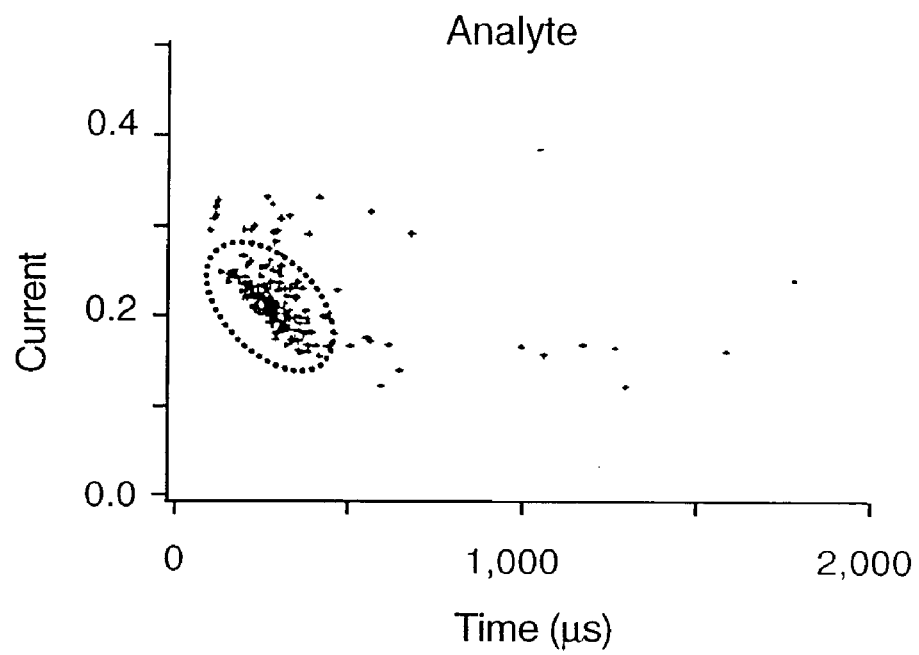
FIGS. 11A–11D and 13A–13C are event plots of time and current.
Figure 11B:
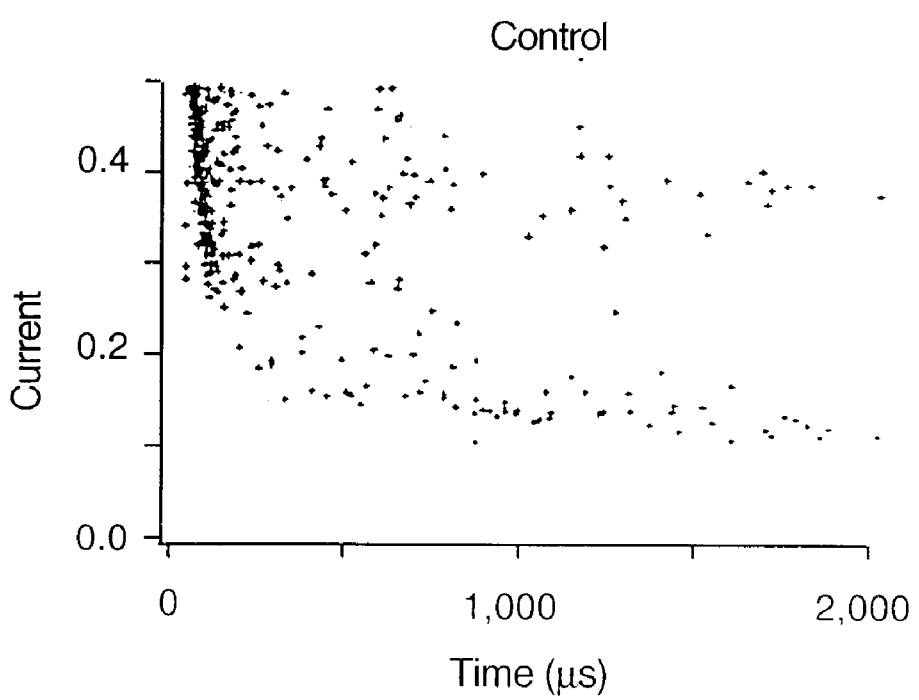
Figure 11C:
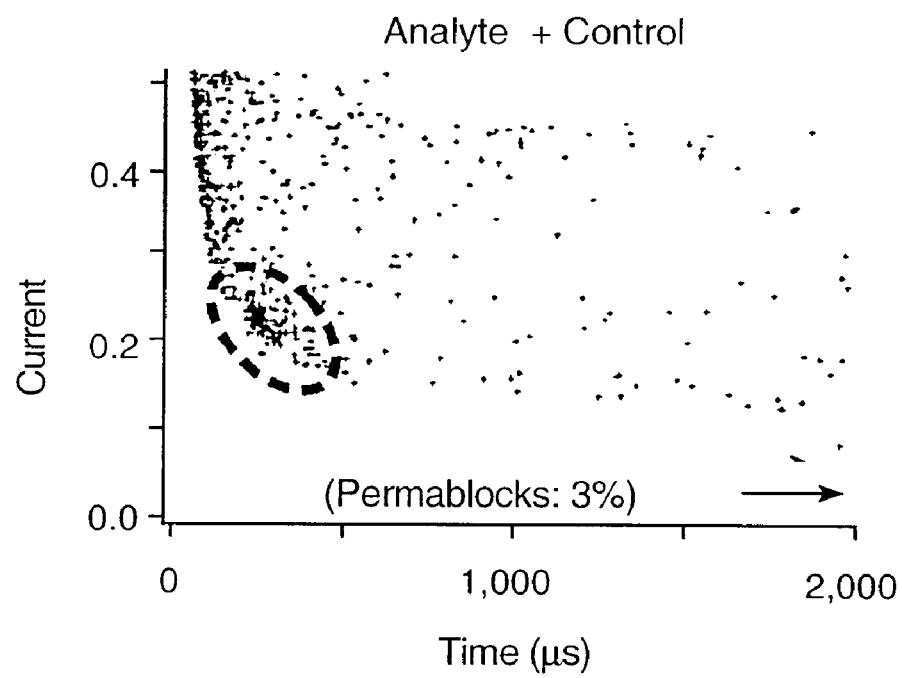
Figure 11D:
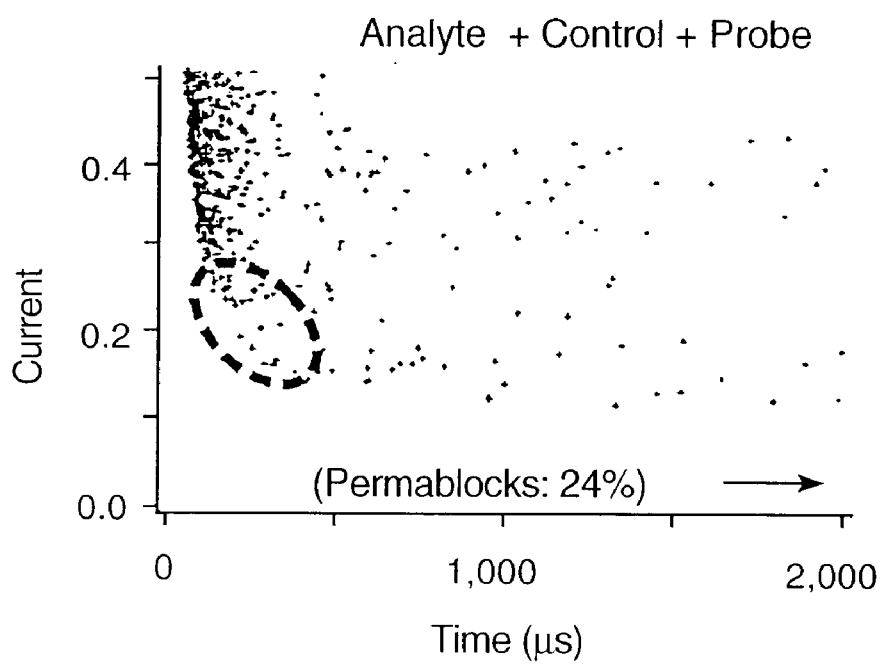

C-3';

b) a matching probe, a short single-stranded polymer containing 23 nucleotides that is expected to hybridize with (a) and having the sequence:

(SEQ ID NO:2)
3'-T GAT GAG GAG TGT GAT GGT ATG G-5';

and c) a control probe, a single-stranded oligomer containing 22 nucleotides that is not expected to hybridize with (a) and having the sequence:

(SEQ ID NO:3)
3'-CTC ACC TAT CCT TCC ACT CAT T-5';

As can be seen in FIGS. 11A–11D, the signals characteristic of the analyte (FIG. 11A) were readily distinguishable from the signals for control probe (FIG. 11B). Further, the signals for a mixture of analyte and control probe did not shift the primary position of the analyte in FIG. 11A, indicating that ability of the analyte to traverse the pore was generally not affected (FIG. 11C) by the presence of a control probe. On the other hand, a mixture of analyte, control probe, and matching probe resulted in an event plot that clearly indicated the ability of the matching probe to shift the plot for analyte, indicating that the probe hybridized to the analyte and affected traversal of the analyte through the pore.

The results in this Example provide the surprising and unexpected observation that single- or double-stranded regions of a nucleic acid can be detected by pore traversal.

It was noted that such signals could be analyzed in a number of ways, depending on the desired purpose of the analysis. First, such assays need not depend exclusively on the change of time required for an analyte to move through the channel. Hybridization could equally well be detected by following the change of time required for the probe to move through the channel. This would make it possible to apply such tests of hybridization using, for example, samples of DNA from airborne or liquid-borne pathogens in a fast, compact, and inexpensive monitoring device for viral pathogens.

An oligonucleotide can readily be created for a target pathogen and mixed with DNA derived from air samples or water samples in the nearby environment to seek out a possible match with nearly single-molecule sensitivity and excellent time resolution. If a match does occur, appropriate circuitry could readily detect the rapid increase or decrease in the relative blockade rate as a function of blockade duration. Once this rate exceeds or diminishes below a pre-determined threshold for a particular blockade duration, the circuit will trigger an appropriate signal to notify the appropriate command centers of a possible threat, and immediate countermeasures can be taken.

Furthermore, a complete analysis of such signals that takes into account the conditions of hybridization (salt, temperature, pH, etc.), the percentage of events whose usual position is shifted, and the peak duration of the events that are shifted to longer duration times, will yield comparative and quantitative estimates of the number of hybridizing molecules (e.g., concentration of the reactants) as well as a measure of the binding energies involved in hybridization.

EXAMPLE 10

Detecting Single Base Mismatch by Varying the Temperature of a Pool of Medium

Figure 12:
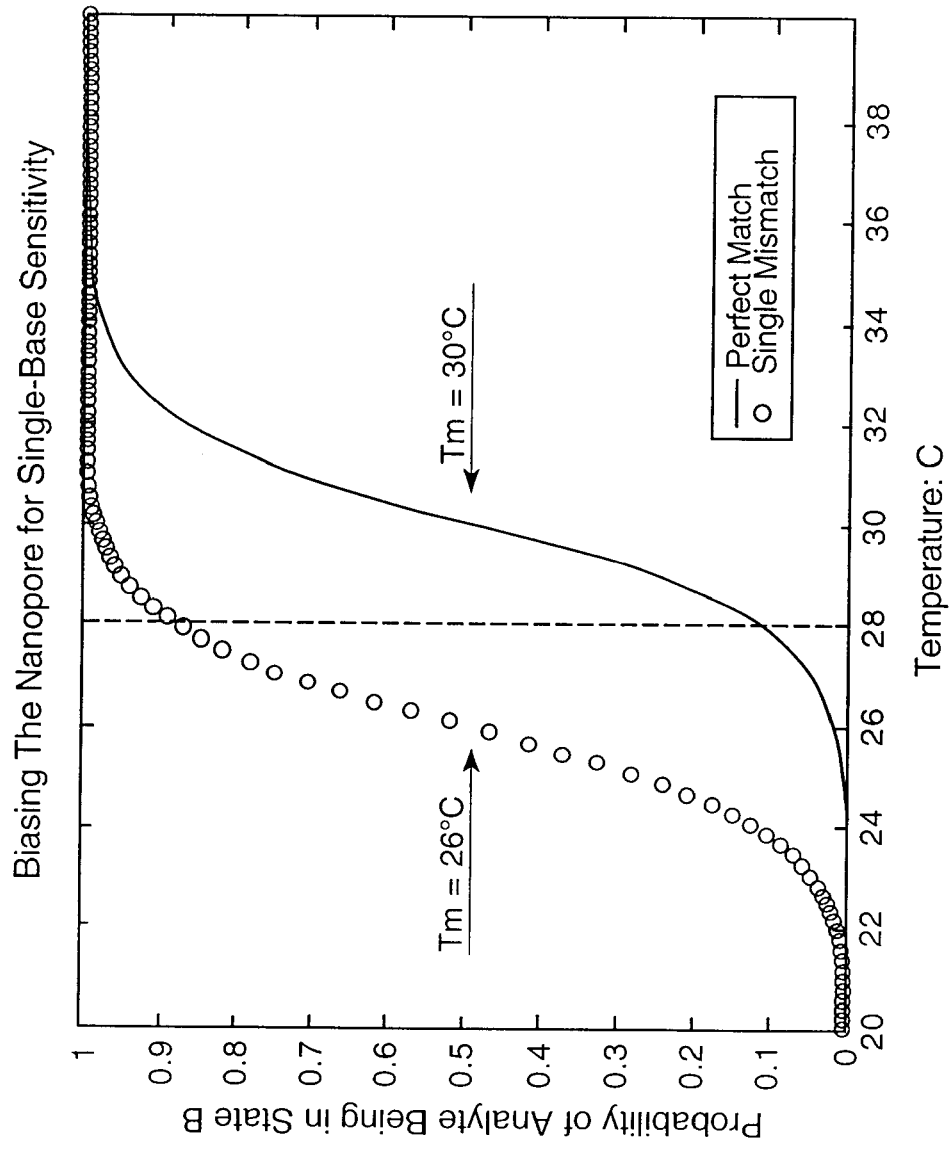
FIG. 12 is a graph showing the probability of a target nucleic acid (analyte) hybridizing to a first probe that is exactly complementary to a portion of the target and a second probe that differs from a target sequence by one nucleotide.

Through adjustment of environmental conditions in Example 9, more detailed information about the analyte's structure can be deduced. In particular, the modulation of temperature can allow for the detection of single-base mutations in an analyte with the proposed hybridization detector. The theoretical foundation for this approach is based on the temperature sensitivity of hybridization with respect to base mismatch. To help understand how this sensitivity can be applied, two states A & B were defined. State A represents the target analyte bound to a short oligomer probe, while state B represents the analyte and oligomer as two independent single-stranded DNA polymers. As illustrated in FIG. 12, the probability of being in state B is small at low temperature, while the probability of being in state B is close to one at high temperature. At an intermediate temperature, defined as the Tm of the probe-analyte pair, the probability of being in state B is one-half. The state of the analyte is easily detected using the nanopore by observing the distribution of events in the event plots at a particular temperature. State A is recognized by the superposition in event plots of the events attributable to free analyte and events attributable to free probe, while state B is detected when the events attributable to free analyte or free probe are shifted to positions of characteristically longer blockades (permablocks). Thus, the observed state information can be used to deduce information about the hybridization characteristics between an analyte and a probe at a specific temperature.

The detection of single base mismatches can be achieved by biasing the temperature of the sample to achieve maximum hybridization sensitivity. The Tm point defined above is known or easily calculated for a particular analyte/probe pair at a specified ionic strength and analyte and probe concentration. The addition of a single base mismatch tends to shift this curve to a lower temperature by 2–4° C., while maintaining the overall shape of the curve. If the temperature of the nanopore environment is then biased to the midpoint between the Tm for the two probes, one being a perfect match and the other having a single base mismatch, then a marked difference in the analyte state is observable using the nanopore, as illustrated in FIG. 12.

The model was validated with an experiment incorporating the α-hemolysin pore as described in Example 9. In this experiment, the following polymers were used:

(a) analyte Px, containing 100 nucleotides with the sequence (SEQ ID NO:4)
5'-CTC ACC TAT CCT TCC ACT CAT TTT CCT TAA CCA

TTT CAT TCA CCC ATC TCA CTA TCA TTA TCT ACA

TCC ATT ACA TCA CTA CTC CTC ACA CTA CCA TAC

C-3';

(b) probe Px0, perfectly complimentary to the 5' end of the analyte, with the sequence 5'-GAG TGG ATA G-3' (SEQ ID NO:5); and (c) probe Px1, complimentary to the 5' end of the analyte except for a single base mismatch (G to C at position 5), with the sequence 5'-GAG TGC ATA G-3'(SEQ ID NO:6).

The Tm for Px0 and Px1 were 30° C. and 26° C., respectively.

Figure 13A:
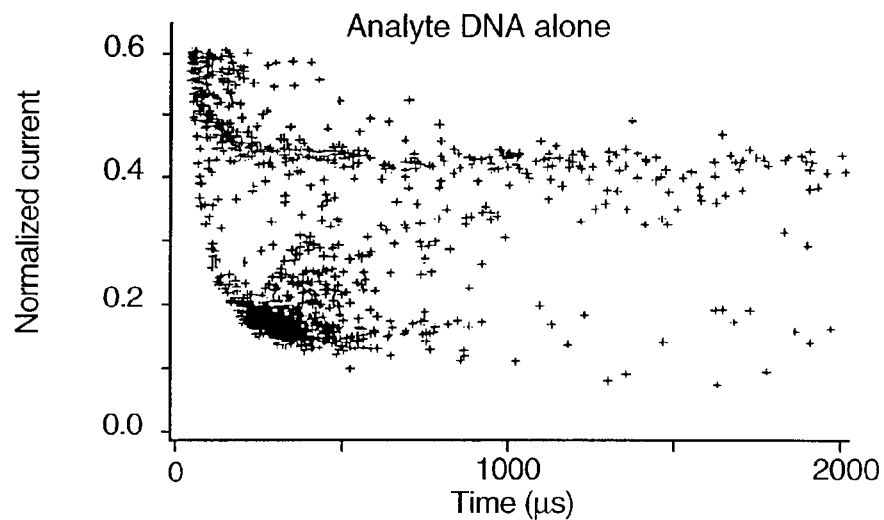
Figure 13B:
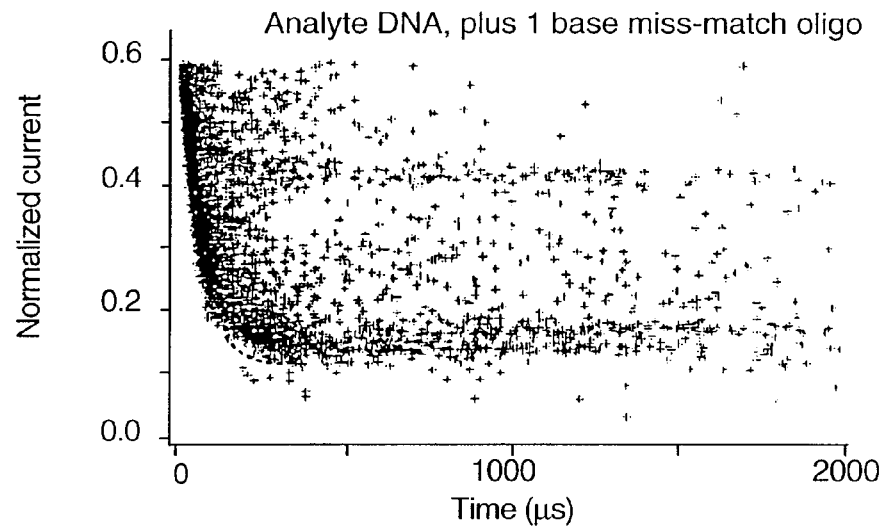
Figure 13C:
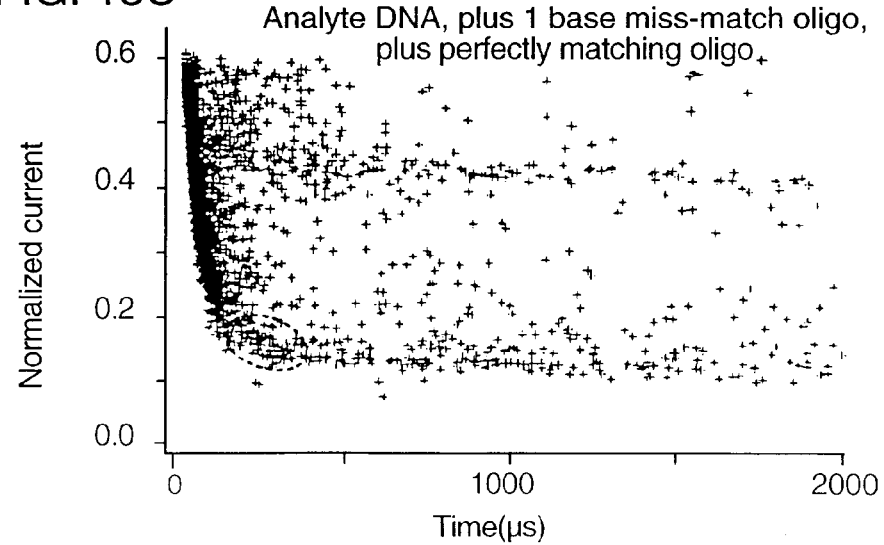

The temperature for the nanopore was then biased to the mean temperature of 28° C. As illustrated in FIGS. 13A–13C, a control was first performed to establish the characteristic region for Px in the event plot of FIG. 13A. Probe Px1 was then added to the solution of Px. The resulting plot in FIG. 13B illustrated two important phenomena: first, the appearance of additional events with the characteristic distribution expected for the shorter 10-base sequence; and second, the maintenance of events (inside broken ellipse) with the distribution expected for Px. Therefore, Px did not interact to a large degree with Px1 at 28° C.

Px0 was then added to the Px/Px1 solution. The event plot in FIG. 13C again illustrated two important phenomena: first, increased counts in the region associated with the 10-mers, due to the addition of Px0; and second, the near extinction of events in the region (inside broken ellipse) associated with Px. The extinction was attributable to the more than 2000 μsec now needed to melt the double-stranded region of the nucleic acid and be pulled through the membrane channel. This observation validated the theoretical expectation that, at a specified bias temperature, an oligomer's hybridization character is easily detectable and that a nanopore can provide a sensitive measure, at single base resolution, of alterations or mutations in an unknown analyte.

The ability to manipulate the environment of the nanopore to resolve single-base mutations makes it possible to apply nanopore technology to the detection of a large number of genetic diseases or pathogens, including cystic fibrosis, HIV, and sickle cell anemia.

II. Polymer Analysis by Detection of Monomers at an Interface

A different embodiment of the invention includes a method of characterizing a linear polymer using 1) an interface, generally created by two immiscible liquids, and 2) a monitoring device such as a force transducer or deflection gauge (e.g., using light) to monitor each monomer of the polymer as it passes across the interface. This embodiment of the sequencing invention is encompassed by pulling a single molecule through the interface formed by two immiscible liquids by either mechanical or electrophoretic means. The force required to pull each successive monomer in the polymer through the interface can be measured, or it may be desirable to monitor physical deflections of the interface or other modifications/interactions of the interface by the monomers to register each successive monomer's move through the interface.

Multiple polymer strands have commonly been pulled through a liquid-air interface as a means of separating and purifying polymers from their surrounding liquor. We propose that polymer chains can be similarly pulled through the interface formed by two immiscible liquids. Both the atomic force microscope and optical tweezers are now routinely used in liquid environments to measure atomic and molecular scale forces and movements. A suitably fine probe attached to a force transducer such as those used in atomic force microscopy or in optical tweezers would advance in Angstrom size steps, and have been used to pull double stranded DNA through DNA solutions. If the force required to pull the different monomers of a polymer through the interface differs from one monomer to another, then measuring the force required to pull each successive monomer through the interface will provide a direct determination of the sequence of monomers in the polymer.

The force required to move a chemical group from one phase to a second, immiscible phase is related to its partition coefficient. For the pertinent polymers that could be sequenced by this technique, the partition coefficient for its monomers would differ from each other. For example, the logarithm of the partition coefficients of the DNA monomers adenine, thymine, guanine, and cytosine in a butanol:water system are, respectively, 2.44, 1.12, 0.45, and −0.68.

A chemical embodiment of this aspect of the invention could be a butanol:water interface, with the underlying aqueous phase containing the polymer to be sequenced. If a fine ceramic, plastic, or metallic probe bearing a suitable charge or chemical group at its tip (e.g., to attract DNA, a positively charged tip; to attract MRNA, oligo dT moieties) is driven through the overlying butanol into the underlying aqueous phase, polymer will stick to the probe tip and be pulled through the interface as the tip is withdrawn from the aqueous phase into the butanol phase. Although the initial strand of material that is pulled through the interface may contain multiple individual polymers, inevitably one single polymer strand will be longer than the others or will have stuck to the probe tip in such a fashion that it will be pulled last, and singly, through the interface. Refinements to the probe tip to increase the likelihood of selecting only one polymer may include decreasing the charge or number of chemical moieties.

Because the energy to pull each of the different monomers of a single polymer chain through the interface will reflect the properties of the monomer, recording the force required to pull a single stranded DNA molecule, for instance, through an interface while maintaining a constant slow movement will in effect record the sequence of the polymer.

An alternative method of measuring the transit of monomers from one phase to the other may be the use of optical means as are known in the art to detect the deflection of the interface caused by each monomer. Due to varying physical properties of the monomer (e.g., size, mass, volume), light may be scattered off the interface in predictable ways for each monomer. For instance, directing a laser at the interface and observing the optical deflection using a bi-cell detector may identify individual monomers by their characteristic deflections of light. Alternatively, pulsed laser techniques may be used, with pulses on the order of $10^{-9}$ to $10^{-12}$ seconds directed at the interface and recorded using a time dependent detector.

What is claimed is:

1. A method of detecting alterations or mutations in a polynucleic acid sequence, comprising:

providing a surface containing a channel of a dimension sufficient to allow sequential monomer-by-monomer passage of a single-stranded polynucleic acid, but not of a double-stranded polynucleic acid;

providing a source of a test polynucleic acid to be analyzed at one side of the surface;

inducing passage of the test polynucleic acid through the channel and monitoring the passage of the test polynucleic acid through the channel; and wherein the method is performed at a temperature that allows a probe to hybridize to the test polynucleic acid if the probe is perfectly complementary to a portion of the polynucleic acid, but increases the probability of no hybridization occurring if the probe varies from being perfectly complementary to the test polynucleic acid.

2. The method of claim 1, wherein the source of the test polynucleic acid comprises an electrically conductive medium.

3. The method of claim 2, wherein inducing the passage of the test polynucleic acid comprises applying a voltage across the interface.

4. The method of claim 3, wherein ionic flow within the channel is monitored.

5. The method of claim 4, wherein duration of an ionic flow blockage is measured.

6. The method of claim 4, wherein magnitude of an ionic flow blockage is measured.

7. The method of claim 1, further comprising:

monitoring passage of the test polynucleic acid through the channel at a first temperature at which the test polynucleotide is unhybridized; and monitoring passage of the test polynucleic acid through the channel at a second temperature at which the test polynucleic acid is hybridized.

8. A method for evaluating a polymer having improved sensitivity, comprising:

providing a surface containing a channel of a dimension sufficient to allow sequential monomer-by-monomer passage of a single-stranded polynucleic acid, but not of a double-stranded polynucleic acid;

providing a polynucleic acid source on one side of the surface, said polynucleic acid source being a hybridized polynucleic acid for which information related to a single strand thereof is desired;

applying a voltage across the channel to induce passage of a single-stranded polynucleic acid through the channel by subjecting the hybridized polynucleic acid to conditions in which the hybridized polynucleic acid undergoes base pair separation (melts) prior to its passage through the channel, such that the passage of the single-stranded polynucleic acid is characterized by higher duration time in the channel or higher ionic current flow through the channel, as compared to conditions suitable for inducing passage of a single-stranded polynucleic acid.

9. A method for evaluating a polymer molecule, the polymer molecule including linearly connected monomer residues, the method comprising:

providing a candidate polymer molecule in a liquid;

providing an interface in contact with the liquid, the interface capable of interacting with the candidate polymer molecule;

causing the candidate polymer molecule to traverse a region of the interface whereby individual monomer residues of the polymer molecule sequentially interact with the interface and data suitable to determine a monomer-dependent characteristic of the polymer molecule are obtained.

10. A method for evaluating a polymer molecule, the polymer molecule including linearly connected monomer residues, the method comprising:

providing a candidate polymer molecule in a liquid; and causing the candidate polymer molecule to traverse an ion permeable passage in an otherwise impermeable barrier in the liquid, whereby individual monomer resides of the polymer molecule sequentially pass across the ion permeable passage and data suitable to determine a monomer-dependant characteristic of the polymer molecule is obtained.

* * * * *

UNITED STATES PATENT AND TRADEMARK OFFICE
CERTIFICATE OF CORRECTION

| | | |
|---|---|---|
| PATENT NO. | : 6,673,615 B2 | Page 1 of 1 |
| APPLICATION NO. | : 10/079178 | |
| DATED | : January 6, 2004 | |
| INVENTOR(S) | : Denison et al. | |

It is certified that error appears in the above-identified patent and that said Letters Patent is hereby corrected as shown below:

Please add the following section in column 1:

Statement as to Federally Sponsored Research
      This invention was made with government support under HG000811 awarded by the National Institutes of Health, MCB-9421831 awarded by the National Science Foundation, and N65236-98-1-5407 awarded by DARPA/Space and Naval Warfare Systems Command. The government has certain rights in the invention.

Signed and Sealed this

Twentieth Day of January, 2009

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,673,615 B2 | |
| APPLICATION NO. | : 10/079178 | |
| DATED | : January 6, 2004 | |
| INVENTOR(S) | : Denison et al. | |

It is certified that error appears in the above-identified patent and that said Letters Patent is hereby corrected as shown below:

Column 1, line 15, Under STATEMENT AS TO FEDERALLY SPONSORED RESEARCH, replace the previous versions with --This invention was made with government support under N65236-98-1-5407 awarded by the U.S. Department of Defense DARPA/Space and Naval Warfare Systems Command. The Government has certain rights in the invention.--.

Signed and Sealed this
Twenty-fourth Day of April, 2012

David J. Kappos
*Director of the United States Patent and Trademark Office*

SEQUENCE LISTING

```
<160> NUMBER OF SEQ ID NOS: 8

<210> SEQ ID NO 1
<211> LENGTH: 100
<212> TYPE: DNA
<213> ORGANISM: Artificial Sequence
<220> FEATURE:
<223> OTHER INFORMATION: analyte

<400> SEQUENCE: 1
ctcacctatc cttccactca ttttccttaa ccatttcatt cacccatctc actatcatta      60
tctacatcca ttacatcact actcctcaca ctaccatacc                          100

<210> SEQ ID NO 2
<211> LENGTH: 23
<212> TYPE: DNA
<213> ORGANISM: Artificial Sequence
<220> FEATURE:
<223> OTHER INFORMATION: matching probe expected to hybridize with the
      analyte of SEQ ID NO. 1

<400> SEQUENCE: 2
ggtatggtag tgtgaggagt agt                                             23

<210> SEQ ID NO 3
<211> LENGTH: 22
<212> TYPE: DNA
<213> ORGANISM: Artificial Sequence
<220> FEATURE:
<223> OTHER INFORMATION: control probe not expected to hybridize with
      the analyte of SEQ ID NO. 1

<400> SEQUENCE: 3
ttactcacct tcctatccac tc                                              22

<210> SEQ ID NO 4
<211> LENGTH: 100
<212> TYPE: DNA
<213> ORGANISM: Artificial Sequence
<220> FEATURE:
<223> OTHER INFORMATION: analyte Px

<400> SEQUENCE: 4
ctcacctatc cttccactca ttttccttaa ccatttcatt cacccatctc actatcatta      60
tctacatcca ttacatcact actcctcaca ctaccatacc                          100

<210> SEQ ID NO 5
```

```
<211> LENGTH: 10
<212> TYPE: DNA
<213> ORGANISM: Artificial Sequence
<220> FEATURE:
<223> OTHER INFORMATION: probe Px0 complimentary to the 5' end of SEQ ID
      NO. 4

<400> SEQUENCE: 5
gagtggatag                                                              10

<210> SEQ ID NO 6
<211> LENGTH: 10
<212> TYPE: DNA
<213> ORGANISM: Artificial Sequence
<220> FEATURE:
<223> OTHER INFORMATION: probe Px1 complimentary to the 5' end of SEQ ID
      NO. 4 except for single base mismatch at position
      5

<400> SEQUENCE: 6
gagtgcatag                                                              10

<210> SEQ ID NO 7
<211> LENGTH: 61
<212> TYPE: DNA
<213> ORGANISM: Artificial Sequence
<220> FEATURE:
<223> OTHER INFORMATION: synthetic

<400> SEQUENCE: 7
aaaaaaaaaa aaaaaaaaaa aaaaaaaaaa aaaaaaaaaa aaaaaaaaaa gcgcactgcg       60
c                                                                       61

<210> SEQ ID NO 8
<211> LENGTH: 60
<212> TYPE: DNA
<213> ORGANISM: Artificial Sequence
<220> FEATURE:
<223> OTHER INFORMATION: synthetic

<400> SEQUENCE: 8
aaaaaaaaaa aaaaaaaaaa aaaaaaaaaa aaaaaaaaaa aaaaaaaaaa aaaaaaaaaa       60
```